(12) United States Patent
Hickman

(10) Patent No.: US 8,491,904 B2
(45) Date of Patent: Jul. 23, 2013

(54) ISOLATION AND PURIFICATION OF ANTI-IL-13 ANTIBODIES USING PROTEIN A AFFINITY CHROMATOGRAPHY

(75) Inventor: Robert K. Hickman, Worcester, MA (US)

(73) Assignee: Abbvie Inc., North Chicago, IL (US)

( * ) Notice: Subject to any disclaimer, the term of this patent is extended or adjusted under 35 U.S.C. 154(b) by 0 days.

(21) Appl. No.: 12/908,502

(22) Filed: Oct. 20, 2010

(65) Prior Publication Data

US 2011/0206687 A1    Aug. 25, 2011

Related U.S. Application Data

(60) Provisional application No. 61/253,411, filed on Oct. 20, 2009.

(51) Int. Cl.
| | | |
|---|---|---|
| *A61K 39/395* | (2006.01) | |
| *A61K 45/00* | (2006.01) | |
| *C07K 16/24* | (2006.01) | |
| *G01N 33/53* | (2006.01) | |
| *G01N 33/537* | (2006.01) | |
| *G01N 33/538* | (2006.01) | |

(52) U.S. Cl.
USPC ............ 424/145.1; 424/85.2; 530/388.23; 436/541; 436/824; 435/7.1

(58) Field of Classification Search
None
See application file for complete search history.

(56) References Cited

U.S. PATENT DOCUMENTS

| | | | | |
|---|---|---|---|---|
| 5,429,746 A | * | 7/1995 | Shadle et al. | 210/635 |
| 2006/0063228 A1 | * | 3/2006 | Kasaian et al. | 435/69.1 |
| 2006/0194953 A1 | * | 8/2006 | Bonnerjea et al. | 530/387.1 |

FOREIGN PATENT DOCUMENTS

| | | |
|---|---|---|
| WO | WO/2007/117490 | 10/2007 |
| WO | WO/2010/048192 | 4/2010 |

OTHER PUBLICATIONS

International Search Report and Written Opinion for PCT/US2010/053388, dated Jul. 19, 2011.
Yang Gaoyun et al., "Therapeutic docing with anti-interlukin-13 monoclonal antibody inhibits asthma progression in mice", *The Journal of Pharmacology and Experimental Therapeutics*, Apr. 2005, 313(1): 8-15, XP002644930.
Tugcu Nihal et al., "Maximizing productivity of chromatography steps for purification of monoclonal antibodies", *Biotechnology and Bioengineering*, Wiley & Sons, Hoboken, NJ, US, Feb. 15, 2008, 99(3): 599-613, XP002556043.
Stein et al., "Cation exchange chromatography in antibody purification: pH screening for optimised binding and HCP removal", Mar. 12, 2007, 848(1): 151-158, XP005922836.
Guse et al., "Purification and analytical characterization of an anti-CD4 monoclonal antibody for human therapy", *Journal of Chromatography*, Elsevier Science Publishers, B.V., NL, Jan. 1, 1994, 661(1-2): 13-23, XP002574060.
Jiskoot et al., "Two-step purification of a murine monoclonal antibody intended for therapeutic application in man", *Journal of Immunological Methods*, Elsevier Science Publishers, B.V., Amsterdam, NL, Nov. 13, 1989, 124(1): 143-156, XP023975129.

\* cited by examiner

*Primary Examiner* — Robert Landsman
*Assistant Examiner* — Bruce D Hissong
(74) *Attorney, Agent, or Firm* — Baker Botts, L.L.P.

(57) ABSTRACT

Disclosed herein are methods for the isolation and purification of anti-IL-13 antibodies wherein the use of an affinity chromatographic step results in an antibody composition sufficiently pure for pharmaceutical uses. The methods described herein comprise pH viral reduction/inactivation, ultrafiltration/diafiltration, affinity chromatography (e.g., Protein A affinity chromatography), ion exchange chromatography, and hydrophobic chromatography. Further, the present invention is directed toward pharmaceutical compositions comprising one or more antibodies of the present invention.

19 Claims, 9 Drawing Sheets

Figure 1.

- Anti-IL-13 Antibody Heavy Chain Variable Region Sequence

```
1          10         20         30         40
EVTLRESGPG LVKPTQTLTL TCTLYGFSLS TSDMGVDWIR
                                   CDR1

QPPGKGLEWL AHIWWDDVKR YNPALKSRLT ISKDTSKNQV
           CDR2

VLKLTSVDPV DTATYYCART VSSGYIYYAM DYWGQGTLVT
                      CDR3

VSS [SEQ ID NO:1]
```

- Anti-IL-13 Antibody Light Chain Variable Region Sequence

```
1          10         20         30         40
DIQMTQSPSS LSASVGDRVT ISCRASQDIR NYLNWYQQKP
                        CDR1

GKAPKLLIFY TSKLHSGVPS RFSGSGSGTD YTLTISSLQP
          CDR2

EDIATYYCQQ GNTLPLTFGG GTKVEIK [SEQ ID NO:2]
       CDR3
```

Figure 2.  Cell Culture Process Flow Diagram

| Cell Culture Step | Set point/target | In-Process Controls Test | Action Limit |
|---|---|---|---|
| Master Cell Bank | Storage temp ≤ -130°C | Viability at thaw | ≥ 80% |
| 1 x 125 mL Disposable Spinner Flask | Temperature 37°C<br>5% $CO_2$ | Culture viability at transfer | ≥ 80% |
| 1 x 125 mL Disposable Spinner Flask | Temperature 37°C<br>5% $CO_2$ | Culture viability at transfer | ≥ 80% |
| 3 x 125 mL Disposable Spinner Flask | Temperature 37°C<br>5% $CO_2$ | Culture viability at transfer | ≥ 80% |
| 1 x 2 L Biowave Bag | Temperature 37°C<br>5% $CO_2$ | Culture viability at transfer | ≥ 80% |
| 1 x 20 L Biowave Bag | Temperature 37°C<br>5% $CO_2$ | Culture viability at transfer | ≥ 80% |
| 2 × 20 L Biowave Bags | Temperature 37°C<br>5% $CO_2$<br>Culture viability at transfer | Culture viability at transfer<br>Viable cell count at transfer<br>Contamination check | ≥ 80%<br>≥ 2.0 × $10^6$/mL<br>No growth |

Figure 2.  Cell Culture Process Flow Diagram (Continued)

| Cell Culture Step | Set point/target | In-Process Controls Test | Action Limit |
|---|---|---|---|
| 110 L Seed Bioreactor | Temperature 37°C<br>pH 7.1<br>40% DO | Viable cell count at transfer<br>Contamination check | $\geq 2.6 \times 10^6$/mL<br>No growth |
| 3000 L Production Bioreactor (Short fill) | Temperature 37°C<br>pH 7.1<br>40% DO | Viable cell count at end of short fill | $\geq 1.6 \times 10^6$/mL |
| 3000 L Production Bioreactor | Temperature 35 → 33°C<br>pH 6.9<br>40% DO | Viable cell count at temperature shift<br>*Daily Samples:*<br>Daily cell count<br>Glucose concentration<br>Poros A HPLC (ABT-308 titer)<br><br>*Harvest sample (unprocessed bulk):*<br>Harvest viability<br>Poros A HPLC (ABT-308 titer)<br>Endotoxin<br>TEM<br><br>Mycoplasma<br>Adventitious viruses<br><br>Q-PCR for MVM<br>Contamination check | $\geq 3.0 \times 10^6$/mL<br><br>Report value<br>Report value<br>Report value<br><br><br>$\leq 50\%$<br>Report value<br>$\leq 5$ EU/mL<br>$\leq 10^8$ virus-like particles/mL<br>Negative[a]<br>No evidence of viral contamination[a]<br>Negative[a]<br>No growth[a] |

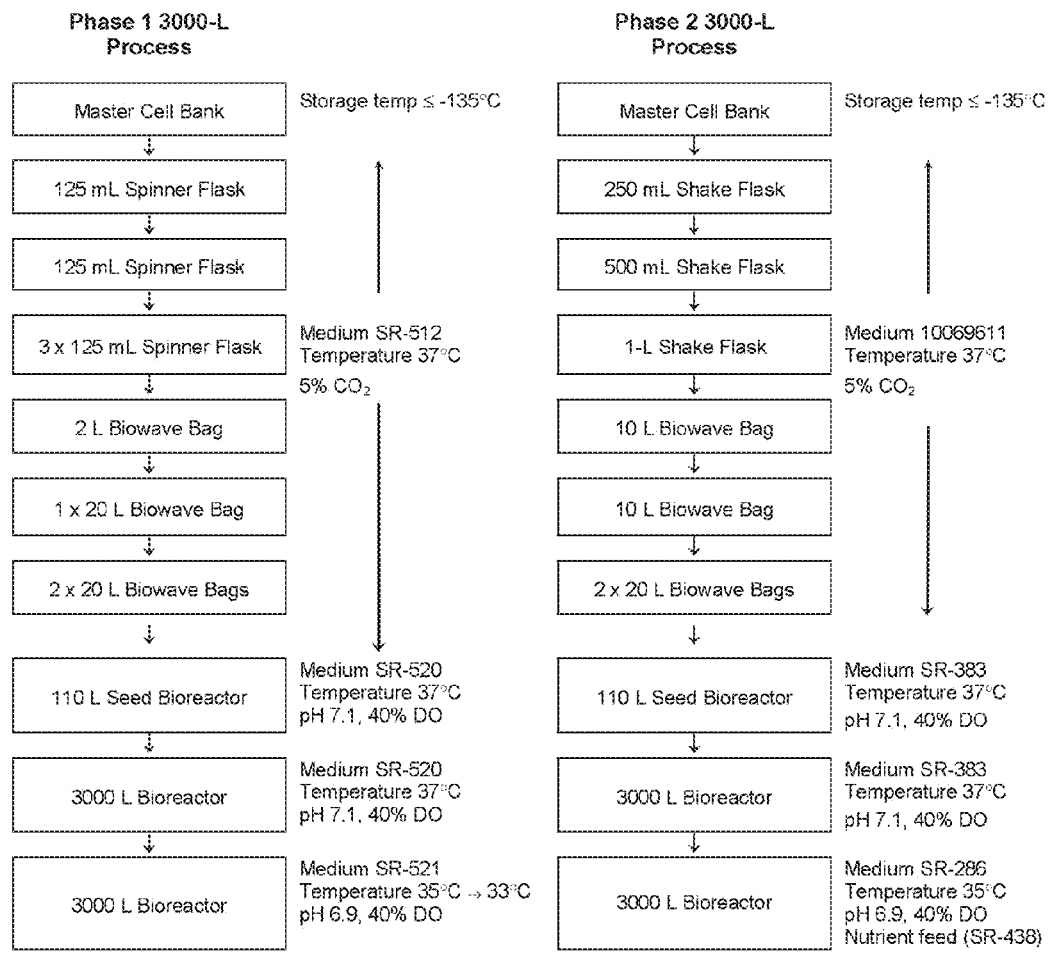
Figure 3. Comparision of Alternative Cell Culture Process Flow Strategies Figure 4.    Primary Recovery and Capture Chromatography Process Flow Diagram

| Step | Set point/target | In-Process Controls Test | Action Limit |
|---|---|---|---|
| Primary Recovery and Harvest Clarification | Ambient temperature<br>10-25 L/min<br>Depth and membrane filters | Poros A HPLC<br>Bioburden[a]<br>Endotoxin[a] | Recorded to calculate mass<br>≤ 15.0 CFU/mL<br>≤ 5 EU/mL |
| Protein A Affinity Chromatography | Ambient temperature<br>45 × 22 cm column (35 L)<br>Flow rate 150 – 300 cm/hr<br>Elution buffer pH 3.5<br>Load ≤ 32 g protein/L resin<br>Hold eluate at ambient | $A_{280}$<br>SE-HPLC<br>Bioburden[a]<br>Endotoxin[a] | Recorded to calculate mass<br>≥ 90.0% Monomer<br>≤ 15.0 CFU/mL<br>≤ 5 EU/mL |
| Low pH Treatment and Filtration | Ambient temperature<br>pH 3.5, 60 - 70 min<br>Adjust to pH 5<br>Depth and membrane filters | $A_{280}$<br>SE-HPLC<br>Bioburden[a]<br>Endotoxin[a] | Recorded to calculate mass<br>≥ 90.0% Monomer<br>≤ 15.0 CFU/mL<br>≤ 5 EU/mL | a. Sample taken at the start of the next unit operation.

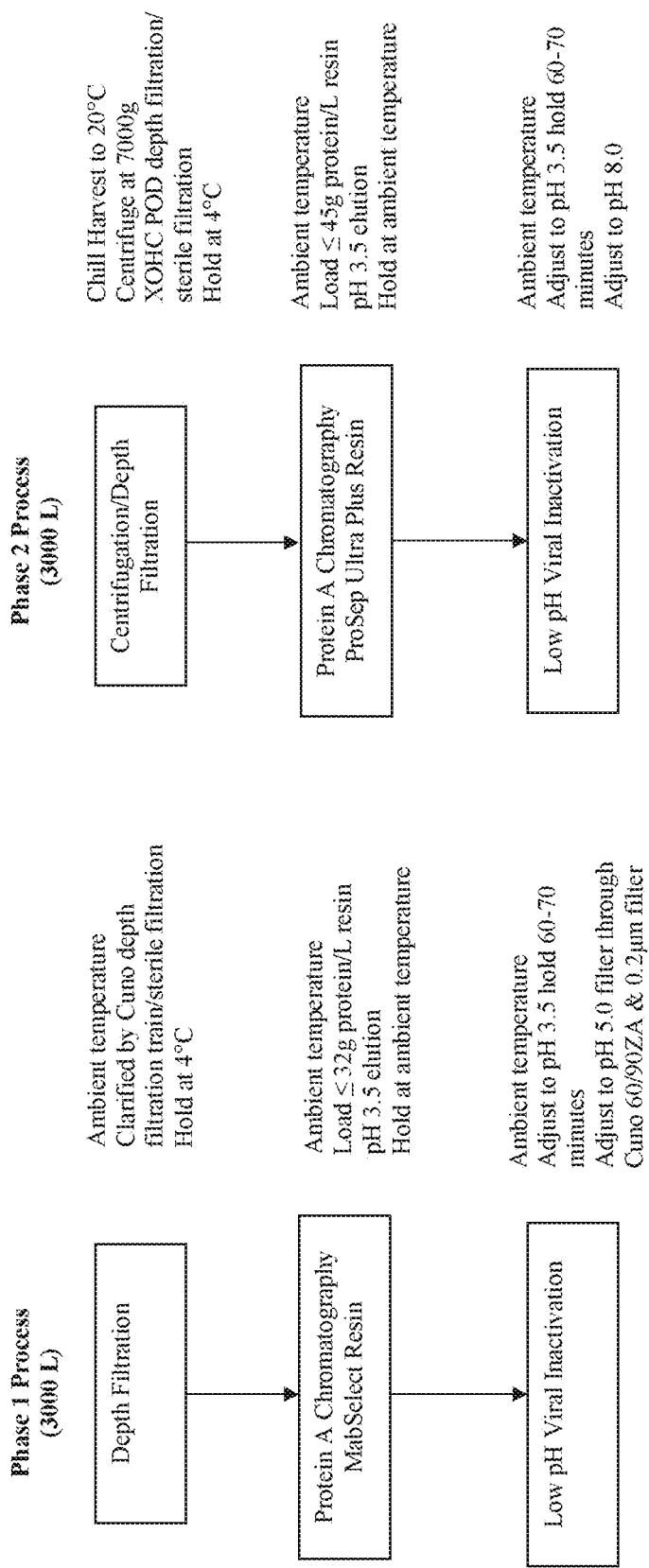
Figure 5. Comparison of Alternative Primary Recovery and Capture Flow Strategies Figure 6. Fine Purification Process Flow Diagram

| Step | Set point/target | In-Process Controls Test | Action Limit |
|---|---|---|---|
| Strong Anion Exchange Chromatography | Temperature 10-14°C | Load $A_{280}$ | Recorded to calculate mass |
| | Adjust to pH 8 | SE-HPLC | ≥ 90.0% Monomer |
| | Adjust conductivity to 5.0 – 6.5 mS/cm | Bioburden[a] | ≤ 15.0 CFU/mL |
| | Delipid and membrane filters | Endotoxin[a] | ≤ 5 EU/mL |
| | 45 × 22 cm column (35 L) | | |
| | Flow rate 100 cm/hr | | |
| | Load ≤ 80 g protein/L resin | | |
| Hydrophobic Interaction Chromatography | Temperature 10-14°C | Load $A_{280}$ | Recorded to calculate mass |
| | 60 × 15 cm column (42 L) | Eluate $A_{280}$ | Recorded to calculate mass |
| | pH 7 | SE-HPLC | ≥ 90.0% Monomer |
| | Flow rate 20 - 75 cm/hr | Bioburden[a] | ≤ 15.0 CFU/mL |
| | Load ≤ 64 g protein/L resin | Endotoxin[a] | ≤ 5 EU/mL |
| Nanofiltration | Temperature 10-14°C | Filtrate $A_{280}$ | Recorded to calculate mass |
| | Pressure ≤ 34 psig | SE-HPLC | ≥ 90.0% monomer |
| | | Bioburden[a] | ≤ 15.0 CFU/mL |
| | | Endotoxin[a] | ≤ 5 EU/mL |
| | | Filter Integrity | ≥ 32.8 mL/min @ 85 psig (UDV20) |
| | | | ≥ 17.0 mL/min @ 85 psig (DV20) | a. Sample taken at the start of the next unit operation.

Figure 6.    Fine Purification Process Flow Diagram (Continued)

| Step | Set point/target | In-Process Controls Test | Action Limit |
|---|---|---|---|
| UF/DF | Temperature 10-14°C | $A_{280}$ | Recorded to calculate mass |
| | Diafilter into 15 mM Histidine, pH 5.6 | SE-HPLC | ≥ 90.0% monomer |
| | Target concentration 120 - 160 g/L | Bioburden[a] | ≤ 15.0 CFU/mL |
| | | Endotoxin[a] | ≤ 5 EU/mL |
| Filter, Bottle And Freeze Drug Substance | Temperature 2-8°C | $A_{280}$ | Recorded to calculate mass |
| | Freeze -80°C (nominal) | Bioburden | ≤ 1 CFU/mL[c] |
| | Concentration 120-160 g/L | Endotoxin[b] | ≤ 0.2 EU/mg[c] |
| | | Filter Integrity[b] | Bubble point ≥ 50 psid | a. Sample taken at the start of the next unit operation.
b. Drug substance test results.
c. Drug substance specifications

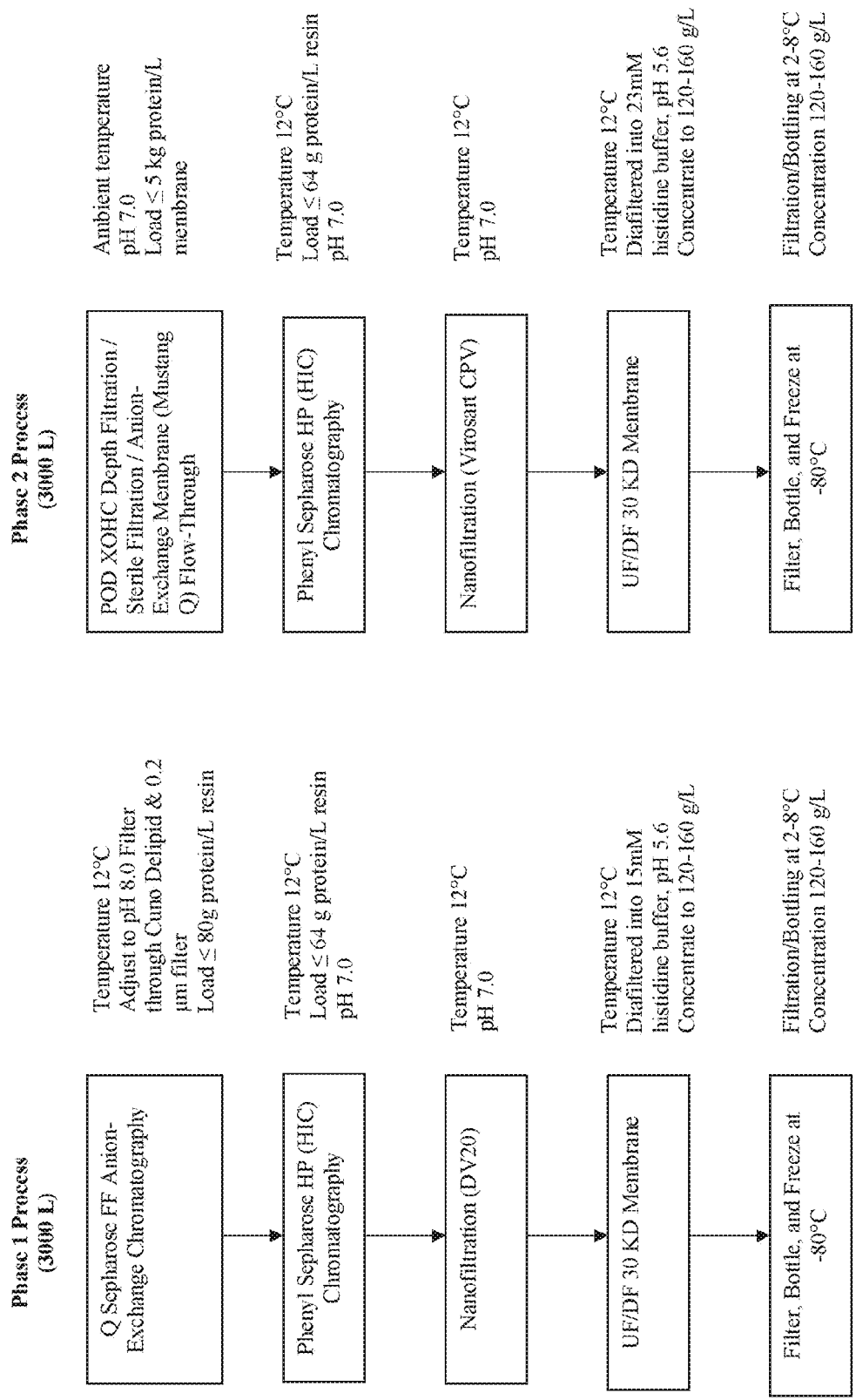
Figure 7. Comparison of Alternative Fine Purification Flow Strategies

ISOLATION AND PURIFICATION OF ANTI-IL-13 ANTIBODIES USING PROTEIN A AFFINITY CHROMATOGRAPHY

CROSS REFERENCE TO RELATED APPLICATION

This application claims the benefit of U.S. Provisional Application Ser. No. 61/253,411, filed Oct. 20, 2009, which is hereby incorporated by reference in its entirety.

SEQUENCE LISTING

The specification further incorporates by reference the Sequence Listing submitted herewith via EFS on May 2, 2011. Pursuant to 37 C.F.R. §1.52(e)(5), the Sequence Listing text file, identified as 003168_0998_Sequence_Listing.txt, is 2,422 bytes and was created on May 2, 2011. The Sequence Listing, electronically filed herewith, does not extend beyond the scope of the specification and thus does not contain new matter.

BACKGROUND OF THE INVENTION

Human IL-13 is a 17-kDa glycoprotein cloned from activated T cells and is produced by activated T cells of the Th2 lineage, ThO and ThI CD4+ T cells, CD8+ T cells, and several non-T cell populations, such as mast cells. (Zurawski and de Vries, 1994 Immunol Today, 15, 19-26). IL-13 promotes immunoglobulin isotype switching to IgE in human B cells (Punnonen, Aversa et al. 1993 Proc Natl Acad Sci USA 90 3730-4) and suppresses of inflammatory cytokine production in both human and mouse (de Waal Malefyt et al., 1993, J Immunol, 151, 6370-81; Doherty et al., 1993, J Immunol, 151, 7151-60). IL-13 binds to its cell surface receptors, IL-13Rα1 and IL-13Rα2. IL-13Rα1 interacts with IL-13 with a low affinity (KD ~10 nM), followed by recruitment of IL-4R to form the high affinity (KD ~0.4 nM) signaling heterodimeric receptor complex (Aman et al., 1996, J Biol Chem, 271, 29265-70; Hilton et al., 1996, Proc Natl Acad Sci USA, 93, 497-501). The IL-4R/IL-13Rα1 complex is expressed on many cell types such as B cells, monocyte/macrophages, dendritic cells, eosinophils, basophils, fibroblasts, endothelial cells, airway epithelial cells, and airway smooth muscle cells (Graber et al., 1998, Eur J Immunol, 28, 4286-98; Murata et al., 1998, Int Immunol, 10, 1103-10; Akaiwa et al., 2001, Cytokine, 13, 75-84). Ligation of the IL-13Rα1/IL-4R receptor complex results in activation of a variety of signal-transduction pathways including signal transducer and activator of transcription (ST AT6) and the insulin receptor substrate-2 (IRS-2) pathways (Wang et al., 1995, Blood, 864218-27; Takeda et al., 1996, J Immunol, 157, 3220-2). The IL-13Rα2 chain alone has a high affinity (KD ~0.25-0.4 nM) for IL-13, and functions as both a decoy receptor negatively regulating IL-13 binding (Donaldson et al., 1998, J Immunol, 161, 2317-24), and a signaling receptor that induces TGF-β synthesis and fibrosis via AP-I pathway in macrophages and possibly other cell types (Fichtner-Feigl, Strober et al. 2006 Nat Med 12 99-106).

Several studies conducted in preclinical animal models for asthma indicate that IL-13 plays an important role in asthma. These data include resistance to asthma in IL-13 knockout mice as well as inhibition of the asthma phenotype with IL-13 antagonists (soluble IL-13 receptors, anti-IL-13 mAbs, etc.) in various mouse models (Wills-Karp and Chiaramonte, 2003, Curr Opin Pulm Med, 9 21-7; Wills-Karp, 2004, Immunol Rev, 202 175-90). Multiple studies have demonstrated that pharmacologic administration of recombinant IL-13 to the lungs of mice as well as guinea pigs induces airway mucus hyper-secretion, eosinophilia and airway hyperresponsiveness ("AHR"; Grunig et al., 1998, Science, 282, 2261-3; Wills-Karp et al., 1998, Science, 282, 2258-61; Kibe et al., 2003, Am J Respir Crit Care Med, 167, 50-6; Vargaftig and Singer, 2003, Am J Physiol Lung Cell Mol Physiol, 284, L260-9; Vargaftig and Singer, 2003, Am J Respir Cell Mol Biol, 28, 410-9). These effects of IL-13 are reproduced in transgenic mouse systems with either constitutive or inducible expression of IL-13 (Zhu et al., 1999, J Clin Invest, 103, 779-88; Zhu et al., 2001, Am J Respir Crit Care Med, 164, S67-70; Lanone et al., 2002, J Clin Invest, 110463-74). Chronic transgenic over-expression of IL-13 also induces subepithelial fibrosis and emphysema. Mice deficient in the IL-13 (and IL-4) signaling molecule STAT6 fail to develop allergen-induced AHR and mucus overproduction (Kuperman et al., 2002, Nat Med, 8, 885-9). Studies using soluble IL-13 receptor fusion protein (sIL-13Rα2Fc) have demonstrated the pivotal role of this cytokine in experimental allergen ovalbumin (OVA)-induced airway disease (Grunig et al., 1998, Science, 282, 2261-3; Wills-Karp et al., 1998, Science, 282, 2258-61; Taube et al., 2002, J Immunol, 169, 6482-9). Efficacy of anti-IL-13 treatment was also demonstrated in a chronic model of murine asthma. In addition to exhibiting features of mucus hyper-secretion and AHR, this model of chronic asthma demonstrates several hallmarks of human disease that are lacking in the more acute models. These include eosinophilia of the lung tissue located in inter-epithelial spaces as well as smooth muscle fibrosis as measured by increases in collagen deposition. The chronic asthma model is induced with repeated aerosol challenges with OVA in OVA-sensitized mice 1×/week for a total of 4 weeks. Anti-IL-13 antibody administered for the final 2 weeks of OVA challenges (from day 36 with efficacy readouts assessed on day 53 of study) significantly inhibited AHR, pulmonary inflammation, goblet cell hyperplasia, mucus hypersecretion, and airway fibrosis (Yang et al., 2005, J Pharmacol Exp Ther, 313, 8-15). IL-13 is implicated in the pathogenesis of human asthma as elevated levels of IL-13 mRNA and protein have been detected in lungs of asthmatic patients, which correlate with severity of the disease (Huang et al., 1995, J Immunol, 155, 2688-94). In addition, human IL-3 genetic polymorphisms, which lead to elevated IL-13 levels, have been identified and are associated with asthma and atopy (Heinzmann et al., 2000, Hum Mol Genet, 9, 549-59; Hoerauf et al., 2002, Microbes Infect, 4, 37-42; Vercelli, 2002, Curr Opin Allergy Clin Immunol, 2, 389-93; Heinzmann et al., 2003, J Allergy Clin Immunol, 112, 735-9; Chen et al., 2004, J Allergy Clin Immunol, 114, 553-60; Vladich et al., 2005, J Clin Invest, 115, 747-54), and elevated IL-13 levels have been detected in the lung of asthma patients (Huang et al., 1995, J Immunol, 155, 2688-94; Arima et al., 2002, J Allergy Clin Immunol, 109, 980-7; Berry et al., 2004, J Allergy Clin Immunol, 114, 1106-9). A genetic linkage between IL-13 and asthma has also been demonstrated as individuals with a polymorphism in the IL-13 gene which causes higher plasma IL-13 levels have an increased risk for atopy and asthma (Wills-Karp, 2000, Respir Res, 1, 19-23).

Due to the role of human IL-13 in a variety of human disorders, therapeutic strategies have been designed to inhibit or counteract IL-13 activity. In particular, antibodies that bind to, and neutralize, IL-13 have been sought as a means to inhibit IL-13 activity. However, there exists a need in the art for improved methods of producing and purifying such antibodies for pharmaceutical use. The present invention addresses this need.

SUMMARY OF THE INVENTION

In certain embodiments, the present invention is directed to purified, isolated antibodies and antibody fragments that bind to IL-13 as well as pharmaceutical compositions comprising such antibodies and fragments. In certain embodiments, the invention pertains to isolated antibodies, or antigen-binding portions thereof, that bind to human IL-13. The isolated anti-IL-13 antibodies of the present invention can be used in a clinical setting as well as in research and development. In certain embodiments, the present invention is directed to an anti-IL-13 antibody comprising the heavy and light chain sequences identified in FIG. 1.

Certain embodiments of the invention are directed toward methods of purifying anti-IL-13 antibodies, or antigen-binding portions thereof, from a sample matrix to render the antibodies substantially free of host cell proteins ("HCPs") and leached Protein A. In certain aspects, the sample matrix (or simply "sample") comprises a cell line employed to produce anti-IL-13 antibodies of the present invention. In particular aspects, the sample comprises a cell line used to produce human anti-IL-13 antibodies.

In certain embodiments the present invention provides for a method of purifying IL-13 antibodies that comprises a primary recovery step to, among other things, remove cells and cellular debris. In certain embodiments of the method, the primary recovery step includes one or more centrifugation or depth filtration steps. For example, and not by way of limitation, such centrifugation steps can be performed at approximately 7000×g to approximately 11,000×g. In addition, certain embodiments of the above-described method will include a depth filtration step, such as a delipid depth filtration step.

In certain embodiments, the primary recovery sample is subjected to an affinity chromatography step. The affinity chromatography step comprises subjecting the primary recovery sample to a column comprising a suitable affinity chromatographic support. Non-limiting examples of such chromatographic supports include, but are not limited to Protein A resin, Protein G resin, affinity supports comprising the antigen against which the antibody of interest was raised, and affinity supports comprising an Fc binding protein. Protein A resin is useful for affinity purification and isolation of antibodies (IgG). In one aspect, a Protein A column is equilibrated with a suitable buffer prior to sample loading. An example of a suitable buffer is a Tris/NaCl buffer, pH around 7.2. Following this equilibration, the sample can be loaded onto the column. Following the loading of the column, the column can be washed one or multiple times using, e.g., the equilibrating buffer. Other washes including washes employing different buffers can be used before eluting the column. The Protein A column can then be eluted using an appropriate elution buffer. An example of a suitable elution buffer is an acetic acid/NaCl buffer, pH around 3.5. The eluate can be monitored using techniques well known to those skilled in the art. For example, the absorbance at $OD_{280}$ can be followed. The eluated fraction(s) of interest can then be prepared for further processing In certain embodiments of the present invention, a low pH adjustment step follows Protein A affinity chromatography. In such embodiments, the Protein A eluate comprising the putative anti-IL-13 antibody, or antigen-binding portion thereof, is subjected to a pH adjustment to a pH of about 3 to about 4. In certain aspects, the pH is adjusted to about 3.5. The low pH, among other things, promotes the reduction and/or inactivation of pH-sensitive viruses that may be contaminating the sample. After a suitable period of time, the pH is adjusted to between about 4.5 and about 6.0, including, but not limited to, about 5.0, and the sample is subjected to further purification steps.

In certain embodiments, an ion exchange step follows either Protein A affinity chromatography or a low pH adjustment step. This ion exchange step can be either cation or anion exchange or a sequential combination of both. This step can be a single ion exchange procedure or can include multiple ion exchange steps such as a cation exchange step followed by an anion exchange step or visa versa. In one aspect, the ion exchange step is a one step procedure. In another aspect, the ion exchange step involves a two step ion exchange process. A suitable cation exchange column is a column whose stationary phase comprises anionic groups. An example of such a column is a Fractogel™ $SO_3^-$. This ion exchange capture chromatography step facilitates the isolation of antibodies from a sample. A suitable anion exchange column is a column whose stationary phase comprises cationic groups. An example of such a column is a Q Sepharose™ column. An alternative is a Pall Mustang Q membrane cartridge. One or more ion exchange step further isolates antibodies by reducing impurities such as host cell proteins and DNA, and, where applicable, affinity matrix protein. This anion exchange procedure is a flow through mode of chromatography wherein the antibodies of interest do not interact or bind to the anion exchange resin (or solid phase). However, many impurities do interact with and bind to the anion exchange resin. In a particular aspect, the ion exchange step is anion exchange chromatography.

The affinity chromatography eluate is prepared for ion exchange chromatography by adjusting the pH and ionic strength of the sample buffer. For example, the affinity eluate can be adjusted to a pH of about 4.5 to about 8.5 in a 1 M Tris buffer. Prior to loading the sample (the affinity eluate) onto the ion exchange column, the column can be equilibrated using a suitable buffer. An example of a suitable buffer is a Tris/NaCl buffer with a pH of about 4.5 to about 8. Following equilibration, the column can be loaded with the affinity eluate. Following loading, the column can be washed one or multiple times with a suitable buffer. An example of a suitable buffer is the equilibration buffer itself. Flow-through collection can commence, e.g., as the absorbance ($OD_{280}$) rises above about 0.2 AU.

In certain embodiments, a first and second ion exchange step is performed following primary recovery or otherwise in the absence of an affinity chromatography step. In certain of such embodiments, the ion exchange sample is subjected to an intermediate filtration step, either prior to the first ion exchange step, between the two ion exchange steps, or both. In certain aspects, this filtration step comprises capture ultrafiltration/diafiltration ("UF/DF"). Among other things, such filtration facilitates the concentration and buffer exchange of anti-IL-13 antibodies and antigen-binding portions thereof.

Certain embodiments of the invention provide for a method comprising one or more hydrophobic interactive chromatography ("HIC") step. A suitable HIC column is one whose stationary phase comprises hydrophobic groups. A non-limiting example of such a column is a Phenyl HP Sepharose™ column. In certain circumstances anti-IL-13 antibodies will form aggregates during the isolation/purification process. Inclusion of one or more HIC step facilitates the reduction or elimination of such aggregations. HIC also assists in the removal of impurities. In certain embodiments the HIC step employs a high salt buffer to promote interaction of the anti-IL-13 antibodies (or aggregations thereof) with the hydrophobic column. The anti-IL-13 antibodies can then be eluted using lower concentrations of salt.

In certain embodiments, the HIC eluate is filtered using a viral removal filter such as, but not limited to, an Ultipor DV50™ filter (Pall Corporation, East Hills, N.Y.). Alternative filters, such as Viresolve™ filters (Millipore, Billerica, Mass.); Zeta Plus VR™ filters (CUNO; Meriden, Conn.); and Planova™ filters (Asahi Kasei Pharma, Planova Division, Buffalo Grove, Ill.), can also be used in such embodiments.

In certain embodiments, the invention is directed to one or more pharmaceutical composition comprising an isolated anti-IL-13 antibody or antigen-binding portion thereof and an acceptable carrier. In one aspect, the composition further comprises one or more antibody or antigen-binding portion thereof in addition to the anti-IL-13 antibody. In another aspect, the compositions further comprise one or more pharmaceutical agents.

The purity of the antibodies of interest in the resultant sample product can be analyzed using methods well known to those skilled in the art, e.g., size-exclusion chromatography, Poros™ A HPLC Assay, HCP ELISA, Protein A ELISA, and western blot analysis.

BRIEF DESCRIPTIONS OF THE DRAWINGS

FIG. 1 discloses the heavy and light chain variable region sequences of a non-limiting example of an anti-IL-13 antibody.

FIG. 2 discloses an exemplary cell culture process flow diagram, including set points, in process control tests, and action limits.

FIG. 3 discloses a comparison of alternative cell culture process flow strategies.

FIG. 4 discloses a primary recovery capture chromatography process flow diagram, including set points, in process control tests, and action limits.

FIG. 5 discloses a comparison of alternative primary recovery and capture flow strategies.

FIG. 6 discloses a fine purification process flow diagram, including set points, in process control tests, and action limits.

FIG. 7 discloses a comparison of alternative fine purification flow strategies.

DETAILED DESCRIPTION OF THE INVENTION

The present invention is directed to antibodies that bind to IL-13. In one aspect, the invention pertains to isolated antibodies, or antigen-binding portions thereof, that bind to human IL-13. The isolated anti-IL-13 antibody of the present invention can be used in a clinical setting as well as in research and development. The present invention also pertains to methods for purifying anti-IL-13 antibodies, or antigen-binding portions thereof. Suitable anti-IL-13 antibodies that may be purified in the context of the instant invention are disclosed in PCT Application No. PCT/US2007/019660, which is hereby incorporated by reference in its entirety, including the antibody that has subsequently been identified as ABT-308. Exemplary anti-IL-13 antibody heavy and light chain sequences are set forth in FIG. 1. The present invention also relates to pharmaceutical compositions comprising the anti-IL-13 antibodies or antigen-binding portions thereof described herein.

For clarity and not by way of limitation, this detailed description is divided into the following sub-portions:
1. Definitions;
2. Antibody Generation;
3. Antibody Production;
4. Antibody Purification;
5. Methods of Assaying Sample Purity;
6. Further Modifications;
7. Pharmaceutical Compositions; and
8. Antibody Uses.

1. Definitions

In order that the present invention may be more readily understood, certain terms are first defined.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or "antibody portion") includes fragments of an antibody that retain the ability to specifically bind to an antigen (e.g., hIL-13). It has been shown that the antigen-binding function of an antibody can be performed by fragments of a full-length antibody. Examples of binding fragments encompassed within the term "antigen-binding portion" of an antibody include (i) a Fab fragment, a monovalent fragment comprising the VL, VH, CL and CH1 domains; (ii) a F(ab')2 fragment, a bivalent fragment comprising two Fab fragments linked by a disulfide bridge at the hinge region; (iii) a Fd fragment comprising the VH and CH1 domains; (iv) a Fv fragment comprising the VL and VH domains of a single arm of an antibody, (v) a dAb fragment (Ward et al., (1989) Nature 341:544-546, the entire teaching of which is incorporated herein by reference), which comprises a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883, the entire teachings of which are incorporated herein by reference). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123, the entire teachings of which are incorporated herein by reference). Still further, an antibody or antigen-binding portion thereof may be part of a larger immunoadhesion molecule, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101, the entire teaching of which is incorporated herein by reference) and use of a cysteine residue, a marker peptide and a C-terminal polyhistidine tag to make bivalent and biotinylated scFv molecules (Kipriyanov, S. M., et al. (1994) Mol. Immunol. 31:1047-1058, the entire teaching of which is incorporated herein by reference). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. In one aspect, the antigen binding portions are complete domains or pairs of complete domains.

The phrase "human interleukin 13" (abbreviated herein as hIL-13, or IL-13), as used herein, refers to a 17-kDa glycoprotein cloned from activated T cells (Zurawski and de Vries, 1994 Immunol Today 15 19-26) and which is produced by activated T cells of the Th2 lineage. ThO and ThI CD4+ T cells, CD8+ T cells, and several non-T cell populations such as mast cells also produce IL-13 (Zurawski and de Vries, 1994 Immunol Today 15 19-26). IL-13 function includes the promotion of immunoglobulin isotype switching to IgE in human B cells (Punnonen, Aversa et al. 1993 Proc Natl Acad Sci USA 90 3730-4) and suppression of inflammatory cytokine production in both human and mouse (de Waal et al., 1993 J Immunol 151 6370-81; Doherty et al., 1993 J Immunol 151 7151-60). IL-13 binds to cell surface receptors identified as IL-13Rα1 and IL-13Rα2. The IL-13Rα1 receptor interacts with IL-13 with a low affinity (KD ~10 nM), followed by recruitment of IL-4R to form the high affinity (KD ~0.4 nM) signaling heterodimeric receptor complex (Aman et al., 1996 J Biol Chem 271 29265-70; Hilton et al., 1996 Proc Natl Acad Sci USA 93 497-501). The IL-4R/IL-13Rα1 complex is expressed on many cell types such as B cells, monocyte/macrophages, dendritic cells, eosinophils, basophils, fibroblasts, endothelial cells, airway epithelial cells, and airway smooth muscle cells (Graber et al., 1998 Eur J Immunol 28 4286-98; Murata et al., 1998 Int Immunol 10 1103-10; Akaiwa et al., 2001 Cytokine 13 75-84). Ligation of the IL-13Rα1/IL-4R receptor complex results in activation of a variety of signal-transduction pathways including signal transducer and activator of transcription (ST AT6) and the insulin receptor substrate-2 (IRS-2) pathways (Wang et al., 1995 Blood 864218-27; Takeda et al., 1996 J Immunol 157 3220-2). The IL-13Rα2 chain alone has a high affinity (KD ~0.25-0.4 nM) for IL-13, and functions as both a decoy receptor negatively regulating IL-13 binding (Donaldson, Whitters et al. 1998 J Immunol 161 2317-24), and as a signaling receptor that induces TGF-b synthesis and fibrosis via AP-I pathway in macrophages and possibly other cell types (Fichtner-Feigl et al., 2006 Nat Med 12 99-106). The nucleic acid encoding IL-13 is available as GenBank Accession No. NM_002188 and the polypeptide sequence is available as GenBank Accession No. NP_002179. The term human IL-13 is intended to include recombinant human IL-13 (rh IL-13), which can be prepared by standard recombinant expression methods.

The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242, the entire teachings of which are incorporated herein by reference). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The term "human antibody" includes antibodies having variable and constant regions corresponding to human germline immunoglobulin sequences as described by Kabat et al. (See Kabat, et al. (1991) Sequences of proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), e.g., in the CDRs and in particular CDR3. The mutations can be introduced using the "selective mutagenesis approach." The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In one embodiment, these replacements are within the CDR regions. However, the term "human antibody", as used herein, is not intended to include antibodies in which CDR sequences derived from the germline of another mammalian species, such as a mouse, have been grafted onto human framework sequences.

The phrase "selective mutagenesis approach" includes a method of improving the activity of an antibody by selecting and individually mutating CDR amino acids at least one suitable selective mutagenesis position, hypermutation, and/or contact position. A "selectively mutated" human antibody is an antibody which comprises a mutation at a position selected using a selective mutagenesis approach. In another aspect, the selective mutagenesis approach is intended to provide a method of preferentially mutating selected individual amino acid residues in the CDR1, CDR2 or CDR3 of the heavy chain variable region (hereinafter H1, H2, and H3, respectively), or the CDR1, CDR2 or CDR3 of the light chain variable region (hereinafter referred to as L1, L2, and L3, respectively) of an antibody. Amino acid residues may be selected from selective mutagenesis positions, contact positions, or hypermutation positions. Individual amino acids are selected based on their position in the light or heavy chain variable region. It should be understood that a hypermutation position can also be a contact position. In one aspect, the selective mutagenesis approach is a "targeted approach". The language "targeted approach" is intended to include a method of mutating selected individual amino acid residues in the CDR1, CDR2 or CDR3 of the heavy chain variable region or the CDR1, CDR2 or CDR3 of the light chain variable region of an antibody in a targeted manner, e.g., a "Group-wise targeted approach" or "CDR-wise targeted approach". In the "Group-wise targeted approach", individual amino acid residues in particular groups are targeted for selective mutations including groups I (including L3 and H3), II (including H2 and L1) and III (including L2 and H1), the groups being listed in order of preference for targeting. In the "CDR-wise targeted approach", individual amino acid residues in particular CDRs are targeted for selective mutations with the order of preference for targeting as follows: H3, L3, H2, L1, H1 and L2. The selected amino acid residue is mutated, e.g., to at least two other amino acid residues, and the effect of the mutation on the activity of the antibody is determined. Activity is measured as a change in the binding specificity/affinity of the antibody, and/or neutralization potency of the antibody. It should be understood that the selective mutagenesis approach can be used for the optimization of any antibody derived from any source including phage display, transgenic animals with human IgG germline genes, human antibodies isolated from human B-cells. The selective mutagenesis approach can be used on antibodies which can not be optimized further using phage display technology. It should be understood that antibodies from any source including phage display, transgenic animals with human IgG germline genes, human antibodies isolated from human B-cells can be subject to back-mutation prior to or after the selective mutagenesis approach.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see, e.g., Taylor, L. D., et al. (1992) Nucl. Acids Res. 20:6287-6295, the entire teaching of which is incorporated herein by reference) or antibodies prepared, expressed, created or isolated by any other means that involves splicing of human immunoglobulin gene sequences to other DNA sequences. Such recombinant human antibodies have variable and constant regions derived from human germline immunoglobulin sequences (see, Kabat, E. A., et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or back-mutation or both.

An "isolated antibody" includes an antibody that is substantially free of other antibodies having different antigenic specificities (e.g., an isolated antibody that specifically binds hIL-13 is substantially free of antibodies that specifically bind antigens other than hIL-13). An isolated antibody that specifically binds hIL-13 may bind IL-13 molecules from other species. Moreover, an isolated antibody may be substantially free of other cellular material and/or chemicals.

A "neutralizing antibody" (or an "antibody that neutralized hIL-13 activity") includes an antibody whose binding to hIL-13 results in inhibition of the biological activity of hIL-13. This inhibition of the biological activity of hIL-13 can be assessed by measuring one or more indicators of hIL-13 biological activity. These indicators of hIL-13 biological activity can be assessed by one or more of several standard in vitro or in vivo assays known in the art.

The term "activity" includes activities such as the binding specificity/affinity of an antibody for an antigen, e.g., an anti-hIL-13 antibody that binds to an IL-13 antigen and/or the neutralizing potency of an antibody, e.g., an anti-hIL-13 antibody whose binding to hIL-13 inhibits the biological activity of hIL-13.

The phrase "surface plasmon resonance" includes an optical phenomenon that allows for the analysis of real-time biospecific interactions by detection of alterations in protein concentrations within a biosensor matrix, e.g., using the B1Acore™ system (Pharmacia Biosensor AB, Uppsala, Sweden and Piscataway, N.J.). For further descriptions, see Jonsson, U., et al. (1993) Ann. Biol. Clin. 51:19-26; Jonsson, U., et al. (1991) Biotechniques 11:620-627; Johnsson, B., el al. (1995) J. Mol. Recognit. 8:125-131; and Johnnson, B., et al. (1991) Anal. Biochem. 198:268-277, the entire teachings of which are incorporated herein.

The term "Koff", as used herein, is intended to refer to the off rate constant for dissociation of an antibody from the antibody/antigen complex.

The term "Kd", as used herein, is intended to refer to the dissociation constant of a particular antibody-antigen interaction.

The phrase "nucleic acid molecule" includes DNA molecules and RNA molecules. A nucleic acid molecule may be single-stranded or double-stranded, but in one aspect is double-stranded DNA.

The phrase "isolated nucleic acid molecule," as used herein in reference to nucleic acids encoding antibodies or antibody portions (e.g., VH, VL, CDR3), e.g. those that bind hIL-13 and includes a nucleic acid molecule in which the nucleotide sequences encoding the antibody or antibody portion are free of other nucleotide sequences encoding antibodies or antibody portions that bind antigens other than hIL-13, which other sequences may naturally flank the nucleic acid in human genomic DNA. Thus, e.g, an isolated nucleic acid of the invention encoding a VH region of an anti-hIL-13 antibody contains no other sequences encoding other VH regions that bind antigens other than, for example, hIL-13. The phrase "isolated nucleic acid molecule" is also intended to include sequences encoding bivalent, bispecific antibodies, such as diabodies in which VH and VL regions contain no other sequences other than the sequences of the diabody.

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "modifying", as used herein, is intended to refer to changing one or more amino acids in the antibodies or antigen-binding portions thereof. The change can be produced by adding, substituting or deleting an amino acid at one or more positions. The change can be produced using known techniques, such as PCR mutagenesis.

The term "about", as used herein, is intended to refer to ranges of approximately 10-20% greater than or less than the referenced value. In certain circumstances, one of skill in the art will recognize that, due to the nature of the referenced value, the term "about" can mean more or less than a 10-20% deviation from that value.

The phrase "viral reduction/inactivation", as used herein, is intended to refer to a decrease in the number of viral particles in a particular sample ("reduction"), as well as a decrease in the activity, for example, but not limited to, the infectivity or ability to replicate, of viral particles in a particular sample ("inactivation"). Such decreases in the number and/or activity of viral particles can be on the order of about 1% to about 99%, including about 20% to about 99%, including about 30% to about 99%, including about 40% to about 99%, including about 50% to about 99%, including about 60% to about 99%, including about 70% to about 99%, including about 80% to 99%, and including about 90% to about 99%. In certain non-limiting embodiments, the amount of virus, if any, in the purified antibody product is less than the ID50 (the amount of virus that will infect 50 percent of a target population) for that virus, it is at least 10-fold less than the ID50 for that virus, or at least 100-fold less than the ID50 for that virus, or at least 1000-fold less than the ID50 for that virus.

The phrase "contact position" includes an amino acid position in the CDR1, CDR2 or CDR3 of the heavy chain variable region or the light chain variable region of an antibody which is occupied by an amino acid that contacts antigen in one of the twenty-six known antibody-antigen structures. If a CDR amino acid in any of the twenty-six known solved structures of antibody-antigen complexes contacts the antigen, then that amino acid can be considered to occupy a contact position. Contact positions have a higher probability of being occupied by an amino acid which contact antigens than in a non-contact position. In one aspect, a contact position is a CDR position which contains an amino acid that contacts antigen in greater than 3 of the 26 structures (>1.5%). In another aspect, a contact position is a CDR position which contains an amino acid that contacts antigen in greater than 8 of the 25 structures (>32%).

2. Antibody Generation

The term "antibody" as used in this section refers to an intact antibody or an antigen binding fragment thereof.

The antibodies of the present disclosure can be generated by a variety of techniques, including immunization of an animal with the antigen of interest followed by conventional monoclonal antibody methodologies e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

One animal system for preparing hybridomas is the murine system. Hybridoma production is a very well-established procedure. Immunization protocols and techniques for isolation of immunized splenocytes for fusion are known in the art. Fusion partners (e.g., murine myeloma cells) and fusion procedures are also known.

An antibody can be a human, a chimeric, or a humanized antibody. Chimeric or humanized antibodies of the present disclosure can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In one non-limiting embodiment, the antibodies of this disclosure are human monoclonal antibodies. Such human monoclonal antibodies directed against IL-13 can be generated using transgenic or transchromosomic mice carrying parts of the human immune system rather than the mouse system. These transgenic and transchromosomic mice include mice referred to herein as the HuMAb Mouse® (Medarex, Inc.), KM Mouse® (Medarex, Inc.), and XenoMouse® (Amgen).

Moreover, alternative transchromosomic animal systems expressing human immunoglobulin genes are available in the art and can be used to raise antibodies of the disclosure, such as anti-IL-13 antibodies. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (e.g., Kuroiwa et al. (2002) Nature Biotechnology 20:889-894 and PCT application No. WO 2002/092812) and can be used to raise anti-IL-13 antibodies of this disclosure.

Recombinant human antibodies of the invention, including, but not limited to, anti-IL-13 antibodies, an antigen binding portion thereof, or anti-IL-13-related antibodies disclosed herein can be isolated by screening of a recombinant combinatorial antibody library, e.g., a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia Recombinant Phage Antibody System™, catalog no. 27-9400-01; and the Stratagene SurfZAP™ phage display kit, catalog no. 240612, the entire teachings of which are incorporated herein), examples of methods and reagents particularly amenable for use in generating and screening antibody display libraries can be found in, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum Antibod Hybridomas 3:81-85; Huse et al. (1989) Science 246:1275-1281; M$_c$Cafferty et al., Nature (1990) 348:552-554; Griffiths et al. (1993) EMBO J 12:725-734; Hawkins et al. (1992) J Mol Biol 226:889-896; Clackson et al. (1991) Nature 352:624-628; Grain et al. (1992) PNAS 89:3576-3580; Garrard et al. (1991) Bio/Technology 9:1373-1377; Hoogenboom et al. (1991) Nuc Acid Res 19:4133-4137; and Barbas et al. (1991) PNAS 88:7978-7982; the entire teachings of which are incorporated herein.

Human monoclonal antibodies of this disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In certain embodiments, the methods of the invention include anti-IL-13 antibodies and antibody portions, anti-IL-13-related antibodies and antibody portions, and human antibodies and antibody portions with equivalent properties to anti-IL-13 antibodies, such as high affinity binding to hIL-13 with low dissociation kinetics and high neutralizing capacity. In one aspect, the invention provides treatment with an isolated human antibody, or an antigen-binding portion thereof, that dissociates from hIL-13 with a Kd of about $1 \times 10^{-8}$ M or less and a Koff rate constant of $1 \times 10^{-3}$ s$^{-1}$ or less, both determined by surface plasmon resonance. In specific non-limiting embodiments, an anti-IL-13 antibody purified according to the invention competitively inhibits binding of ABT-308 to IL-13 under physiological conditions.

In yet another embodiment of the invention, antibodies or fragments thereof, such as but not limited to anti-IL-13 antibodies or fragments thereof, can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see, e.g., Canfield and Morrison (1991) J. Exp. Med. 173:1483-1491; and Lund et al. (1991) J. of Immunol. 147:2657-2662, the entire teachings of which are incorporated herein). Reduction in FcR binding ability of the antibody may also reduce other effector functions which rely on FcR interactions, such as opsonization and phagocytosis and antigen-dependent cellular cytotoxicity.

3. Antibody Production
3.1 General Production Strategies

To express an antibody of the invention, DNAs encoding partial or full-length light and heavy chains are inserted into one or more expression vector such that the genes are operatively linked to transcriptional and translational control sequences. (See, e.g., U.S. Pat. No. 6,914,128, the entire teaching of which is incorporated herein by reference.) In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into a separate vector or, more typically, both genes are inserted into the same expression vector. The antibody genes are inserted into an expression vector by standard methods (e.g., ligation of complementary restriction sites on the antibody gene fragment and vector, or blunt end ligation if no restriction sites are present). Prior to insertion of the antibody or antibody-related light or heavy chain sequences, the expression vector may already carry antibody constant region sequences. For example, one approach to converting the anti-IL-13 antibody or anti-IL-13 antibody-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, a recombinant expression vector of the invention can carry one or more regulatory sequence that controls the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, e.g., in Goeddel; Gene Expression Technology: Methods in Enzymology 185, Academic Press, San Diego, Calif. (1990), the entire teaching of which is incorporated herein by reference. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al., the entire teachings of which are incorporated herein by reference.

In addition to the antibody chain genes and regulatory sequences, a recombinant expression vector of the invention may carry one or more additional sequences, such as a sequence that regulates replication of the vector in host cells (e.g., origins of replication) and/or a selectable marker gene. The selectable marker gene facilitates selection of host cells into which the vector has been introduced (see e.g., U.S. Pat. Nos. 4,399,216, 4,634,665 and 5,179,017, all by Axel et al., the entire teachings of which are incorporated herein by reference). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in dhfr-host cells with methotrexate selection/amplification) and the neo gene (for G418 selection).

An antibody, or antibody portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel et al. (eds.) Current Protocols in Molecular Biology, Greene Publishing Associates, (1989) and in U.S. Pat. Nos. 4,816,397 & 6,914,128, the entire teachings of which are incorporated herein.

For expression of the light and heavy chains, the expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, such as mammalian host cells, is suitable because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss and Wood (1985) Immunology Today 6:12-13, the entire teaching of which is incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, e.g., Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

Suitable mammalian host cells for expressing the recombinant antibodies of the invention include Chinese Hamster Ovary (CHO cells) (including dhfr-CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2), the entire teachings of which are incorporated herein by reference.

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce an antibody may be cultured in a variety of media. Commercially available media such as Ham's F10™ (Sigma), Minimal Essential Medium™ ((MEM), (Sigma), RPMI-1640 (Sigma), and Dulbecco's Modified Eagle's Medium™ ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. No. 4,767,704; 4,657,866; 4,927,762; 4,560,655; or 5,122,469; WO 90/03430; WO 87/00195; or U.S. Pat. No. Re. 30,985 may be used as culture media for the host cells, the entire teachings of which are incorporated herein by reference. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Host cells can also be used to produce portions of intact antibodies, such as Fab fragments or scFv molecules. It is understood that variations on the above procedure are within the scope of the present invention. For example, in certain embodiments it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to IL-13, specifically hIL-13. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than IL-13 by crosslinking an antibody of the invention to a second antibody by standard chemical crosslinking methods.

In a suitable system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

When using recombinant techniques, the antibody can be produced intracellularly, in the periplasmic space, or directly secreted into the medium. In one aspect, if the antibody is produced intracellularly, as a first step, the particulate debris, either host cells or lysed cells (e.g., resulting from homogenization), can be removed, e.g., by centrifugation or ultrafiltration. Where the antibody is secreted into the medium, supernatants from such expression systems can be first concentrated using a commercially available protein concentration filter, e.g., an Amicon™ or Millipore Pellicon™ ultrafiltration unit.

Prior to the process of the invention, procedures for purification of antibodies from cell debris initially depend on the site of expression of the antibody. Some antibodies can be secreted directly from the cell into the surrounding growth media; others are made intracellularly. For the latter antibodies, the first step of a purification process typically involves: lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. Where the antibody is secreted, supernatants from such expression systems are generally first concentrated using a commercially available protein concentration filter, e.g., an Amicon™ or Millipore Pellicon™ ultrafiltration unit. Where the antibody is secreted into the medium, the recombinant host cells can also be separated from the cell culture medium, e.g., by tangential flow filtration. Antibodies can be further recovered from the culture medium using the antibody purification methods of the invention.

3.2. Exemplary Production Strategy

In certain embodiments, the initial step of anti-IL-13 antibody production involves the use of spinner flask and Biowave bag operations to expand anti-IL-13 antibody-expressing CHO cells from a single frozen vial to the desired biomass for the inoculation of a 110 L seed bioreactor. A frozen vial of Master Cell Bank CHO cells is thawed and placed in growth medium (SR-512) and centrifuged. The cells are re-suspended in growth medium and expanded at 37° C. and 5% $CO_2$ in disposable spinner flasks, shake flasks, and/or Biowave bags of increasing volume. Duplicate 20 L wave bags are used to maximize the final cell mass expansion prior to inoculation into the seed bioreactor. When the cell density reaches $2.0 \times 10^6$ viable cells/mL from both 20 L wave bags at approximately 15-17 days, the culture is transferred into a 110 L seed bioreactor charged with growth medium SR-520 for further expansion. After inoculation, the target temperature is 37° C., and the pH is set at a target of 7.1 and controlled by addition of NaOH and $CO_2$ sparging. Dissolved oxygen (DO) in the bioreactor is controlled at target value of 40% by sparging with air and oxygen. Once the cell density reaches $\geq 2.6 \times 10^6$ viable cells/mL after approximately 2-4 days, the culture is transferred into a 3000 L production bioreactor.

In certain embodiments, a partial fill of a 3000 L production bioreactor is used to further expand the cell culture. Initially, the reactor is charged with growth medium (SR-520) and inoculated with the batch from the 110 L seed bioreactor. During this short-fill stage, temperature, dissolved oxygen, and pH are controlled at 37° C., 40%, and 7.1, respectively. The culture pH is controlled with $CO_2$ sparging and NaOH addition. Typically, the cells grow for 2-4 days before reaching the production stage density of $\geq 1.6 \times 10^6$ viable cells/mL.

Production medium SR-521 (1950 L) is added to the cell culture in the 3000 L bioreactor to initiate the production stage. Antifoam C is added to decrease foaming. The culture pH is controlled at a target value of 6.9 with on-off $CO_2$ sparging and NaOH addition. Temperature and dissolved oxygen are controlled at target values of 35° C. and 40%, respectively. The DO in the bioreactor is initially controlled at the desired value by air sparging and supplemented with pure oxygen if needed. In certain embodiments the temperature is lowered to a target value of 33° C. when the viable cell density reaches $3.0 \times 10^6$ cells/mL, and the pH and DO are maintained at target values of 6.9 and 40%, respectively, while in other embodiments the 35° C. target value is maintained. Glucose (SR-334) is added as needed. Cultures are harvested and purified as outlined below when the cell viability drops to 50%.

4. Antibody Purification 4.1 Antibody Purification Generally

The invention provides methods for producing a purified (or "HCP-reduced") antibody preparation from a mixture comprising an antibody and at least one HCP. The present invention also provides methods wherein the final purified preparation is reduced in leached Protein A. The purification process of the invention begins at the separation step when the antibody has been produced using methods described above and conventional methods in the art. Table 1 summarizes one embodiment of a purification scheme. Variations of this scheme, including, but not limited to, variations where the Protein A affinity chromatography step is omitted or the order of the ion exchange steps is reversed, are envisaged and are within the scope of this invention.

TABLE 1

Purification steps with their associated purpose

| Purification step | Purpose |
| --- | --- |
| Primary recovery | clarification of sample matrix |
| Affinity chromatography | antibody capture, host cell protein and associated impurity reduction |
| Low pH incubation | viral reduction/inactivation |
| Anion exchange chromatography | antibody capture, host cell protein and associated impurity reduction |
| Hydrophobic interaction chromatography | reduction of antibody aggregates and host cell proteins |
| Viral filtration | removal of large viruses, if present |
| ultrafiltration/diafiltration | concentration and buffer exchange |
| Final filtration | concentrate and formulate antibody |

Once a clarified solution or mixture comprising the antibody has been obtained, separation of the antibody from the other proteins produced by the cell, such as HCPs, is performed using a combination of different purification techniques, including ion exchange separation step(s) and hydrophobic interaction separation step(s). The separation steps separate mixtures of proteins on the basis of their charge, degree of hydrophobicity, or size. In one aspect of the invention, separation is performed using chromatography, including cationic, anionic, and hydrophobic interaction. Several different chromatography resins are available for each of these techniques, allowing accurate tailoring of the purification scheme to the particular protein involved. The essence of each of the separation methods is that proteins can be caused either to traverse at different rates down a column, achieving a physical separation that increases as they pass further down the column, or to adhere selectively to the separation medium, being then differentially eluted by different solvents. In some cases, the antibody is separated from impurities when the impurities specifically adhere to the column and the antibody does not, i.e., the antibody is present in the flow through.

As noted above, accurate tailoring of a purification scheme relies on consideration of the protein to be purified. In certain embodiments, the separation steps of the instant invention are employed to separate an antibody from one or more HCPs. Antibodies that can be successfully purified using the methods described herein include, but are not limited to, human $IgA_1$, $IgA_2$, IgD, IgE, $IgG_1$, $IgG_2$, $IgG_3$, $IgG_4$, and IgM antibodies. In certain embodiments, the purification strategies of the instant invention exclude the use of Protein A affinity chromatography, for example in the context of the purification of $IgG_3$ antibodies, as $IgG_3$ antibodies bind to Protein A inefficiently. Other factors that allow for specific tailoring of a purification scheme include, but are not limited to: the presence or absence of an Fc region (e.g., in the context of full length antibody as compared to an Fab fragment thereof) because Protein A binds to the Fc region; the particular germline sequences employed in generating to antibody of interest; and the amino acid composition of the antibody (e.g., the primary sequence of the antibody as well as the overall charge/hydrophobicity of the molecule). Antibodies sharing one or more characteristic can be purified using purification strategies tailored to take advantage of that characteristic.

4.2 Primary Recovery

The initial steps of the purification methods of the present invention involve the first phase of clarification and primary recovery of antibody from a sample matrix. In addition, the primary recovery process can also be a point at which to reduce or inactivate viruses that can be present in the sample matrix. For example, any one or more of a variety of methods of viral reduction/inactivation can be used during the primary recovery phase of purification including heat inactivation (pasteurization), pH inactivation, solvent/detergent treatment, UV and γ-ray irradiation and the addition of certain chemical inactivating agents such as β-propiolactone or e.g., copper phenanthroline as in U.S. Pat. No. 4,534,972, the entire teaching of which is incorporated herein by reference. In certain embodiments of the present invention, the sample matrix is exposed to pH viral reduction/inactivation during the primary recovery phase.

Methods of pH viral reduction/inactivation include, but are not limited to, incubating the mixture for a period of time at low pH, and subsequently neutralizing the pH and removing particulates by filtration. In certain embodiments the mixture will be incubated at a pH of between about 2 and 5, at a pH of between about 3 and 4, including, but not limited to, at a pH of about 3.5. The pH of the sample mixture may be lowered by any suitable acid including, but not limited to, citric acid, acetic acid, caprylic acid, or other suitable acids. The choice of pH level largely depends on the stability profile of the antibody product and buffer components. It is known that the quality of the target antibody during low pH virus reduction/inactivation is affected by pH and the duration of the low pH incubation. In certain embodiments the duration of the low pH incubation will be from 0.5 hr to 2 hr, including, but not limited to, 0.5 hr to 1.5 hr, and including, but not limited to, durations of about 1 hr. Virus reduction/inactivation is dependent on these same parameters in addition to protein concentration, which may limit reduction/inactivation at high concentrations. Thus, the proper parameters of protein concentration, pH, and duration of reduction/inactivation can be selected to achieve the desired level of viral reduction/inactivation.

In certain embodiments viral reduction/inactivation can be achieved via the use of suitable filters. A non-limiting example of a suitable filter is the Ultipor DV50™ filter from Pall Corporation. Although certain embodiments of the present invention employ such filtration during the primary recovery phase, in other embodiments it is employed at other phases of the purification process, including as either the penultimate or final step of purification. In certain embodiments, alternative filters are employed for viral reduction/inactivation, such as, but not limited to, Viresolve™ filters (Millipore, Billerica, Mass.); Zeta Plus VR™ filters (CUNO; Meriden, Conn.); and Planova™ filters (Asahi Kasei Pharma, Planova Division, Buffalo Grove, Ill.).

In those embodiments where viral reduction/inactivation is employed, the sample mixture can be adjusted, as needed, for further purification steps. For example, following low pH viral reduction/inactivation the pH of the sample mixture is typically adjusted to a more neutral pH, e.g., from about 4.5 to about 8.5, and including, but not limited to, about 4.9, prior to continuing the purification process. Additionally, the mixture may be flushed with water for injection (WFI) to obtain a desired conductivity.

In certain embodiments, the primary recovery will include one or more centrifugation steps to further clarify the sample matrix and thereby aid in purifying the anti-IL-13 antibodies. Centrifugation of the sample can be run at, for example, but not by way of limitation, 7,000×g to approximately 12,750× g. In the context of large scale purification, such centrifugation can occur on-line with a flow rate set to achieve, for example, but not by way of limitation, a turbidity level of 150 NTU in the resulting supernatant. Such supernatant can then be collected for further purification.

In certain embodiments, the primary recovery will include the use of one or more depth filtration steps to further clarify the sample matrix and thereby aid in purifying the antibodies of the present invention. Depth filters contain filtration media having a graded density. Such graded density allows larger particles to be trapped near the surface of the filter while smaller particles penetrate the larger open areas at the surface of the filter, only to be trapped in the smaller openings nearer to the center of the filter. In certain embodiments the depth filtration step can be a delipid depth filtration step. Although certain embodiments employ depth filtration steps only during the primary recovery phase, other embodiments employ depth filters, including delipid depth filters, during one or more additional phases of purification. Non-limiting examples of depth filters that can be used in the context of the instant invention include the Cuno™ model 30/60ZA depth filters (3M Corp.), and 0.45/0.2 μm Sartopore™ bi-layer filter cartridges.

4.3 Affinity Chromatography

In certain embodiments, the primary recovery sample is subjected to affinity chromatography to further purify the antibody of interest away from HCPs. In certain embodiments the chromatographic material is capable of selectively or specifically binding to the antibody of interest. Non-limiting examples of such chromatographic material include: Protein A, Protein G, chromatographic material comprising the antigen bound by the antibody of interest, and chromatographic material comprising an Fc binding protein. In specific embodiments, the affinity chromatography step involves subjecting the primary recovery sample to a column comprising a suitable Protein A resin. Protein A resin is useful for affinity purification and isolation of a variety antibody isotypes, particularly $IgG_1$, $IgG_2$, and $IgG_4$. Protein A is a bacterial cell wall protein that binds to mammalian IgGs primarily through their Fc regions. In its native state, Protein A has five IgG binding domains as well as other domains of unknown function.

There are several commercial sources for Protein A resin. Suitable resins include, but are not limited to, MabSelect™ from GE Healthcare and ProSep Ultra Plus™ from Millipore. A non-limiting example of a suitable column packed with MabSelect™ is an about 1.0 cm diameter×about 21.6 cm long column (~17 mL bed volume). This size column can be used for small scale purifications and can be compared with other columns used for scale ups. For example, a 20 cm×21 cm column whose bed volume is about 6.6 L can be used for larger purifications. Regardless of the column, the column can be packed using a suitable resin such as MabSelect™ or ProSep Ultra Plus™

In certain embodiments it will be advantageous to identify the dynamic binding capacity (DBC) of the Protein A resin in order to tailor the purification to the particular antibody of interest. For example, but not by way of limitation, the DBC of a MabSelect™ or a ProSept Ultra Plus™ column can be determined either by a single flow rate load or dual-flow load strategy. The single flow rate load can be evaluated at a velocity of about 300 cm/hr throughout the entire loading period. The dual-flow rate load strategy can be determined by loading the column up to about 35 mg protein/mL resin at a linear velocity of about 300 cm/hr, then reducing the linear velocity by half to allow longer residence time for the last portion of the load.

In certain embodiments, the Protein A column can be equilibrated with a suitable buffer prior to sample loading. A non-limiting example of a suitable buffer is a Tris/NaCl buffer, pH of about 7.2. A non-limiting example of suitable equilibration conditions is 25 mM Tris, 100 mM NaCl, pH of about 7.2. Following this equilibration, the sample can be loaded onto the column. Following the loading of the column, the column can be washed one or multiple times using, e.g., the equilibrating buffer. Other washes, including washes employing different buffers, can be employed prior to eluting the column. For example, the column can be washed using one or more column volumes of 20 mM citric acid/sodium citrate, 0.5 M NaCl at pH of about 6.0. This wash can optionally be followed by one or more washes using the equilibrating buffer. The Protein A column can then be eluted using an appropriate elution buffer. A non-limiting example of a suitable elution buffer is an acetic acid/NaCl buffer, pH of about 3.5. Suitable conditions are, e.g., 0.1 M acetic acid, pH of about 3.5. The eluate can be monitored using techniques well known to those skilled in the art. For example, the absorbance at $OD_{280}$ can be followed. Column eluate can be collected starting with an initial deflection of about 0.5 AU to a reading of about 0.5 AU at the trailing edge of the elution peak. The elution fraction(s) of interest can then be prepared for further processing. For example, the collected sample can be titrated to a pH of about 5.0 using Tris (e.g., 1.0 M) at a pH of about 10. Optionally, this titrated sample can be filtered and further processed.

4.4 Ion Exchange Chromatography

In certain embodiments, the instant invention provides methods for producing a HCP-reduced antibody preparation from a mixture comprising an antibody and at least one HCP by subjecting the mixture to at least one ion exchange separation step such that an eluate comprising the antibody is obtained. Ion exchange separation includes any method by which two substances are separated based on the difference in their respective ionic charges, and can employ either cationic exchange material or anionic exchange material.

The use of a cationic exchange material versus an anionic exchange material is based on the overall charge of the protein. Therefore, it is within the scope of this invention to employ an anionic exchange step prior to the use of a cationic exchange step, or a cationic exchange step prior to the use of an anionic exchange step. Furthermore, it is within the scope of this invention to employ only a cationic exchange step, only an anionic exchange step, or any serial combination of the two.

In performing the separation, the initial antibody mixture can be contacted with the ion exchange material by using any of a variety of techniques, e.g., using a batch purification technique or a chromatographic technique.

For example, in the context of batch purification, ion exchange material is prepared in, or equilibrated to, the desired starting buffer. Upon preparation, or equilibration, a slurry of the ion exchange material is obtained. The antibody solution is contacted with the slurry to adsorb the antibody to be separated to the ion exchange material. The solution comprising the HCP(s) that do not bind to the ion exchange material is separated from the slurry, e.g., by allowing the slurry to settle and removing the supernatant. The slurry can be subjected to one or more wash steps. If desired, the slurry can be contacted with a solution of higher conductivity to desorb HCPs that have bound to the ion exchange material. In order to elute bound polypeptides, the salt concentration of the buffer can be increased.

Ion exchange chromatography may also be used as an ion exchange separation technique. Ion exchange chromatography separates molecules based on differences between the overall charge of the molecules. For the purification of an antibody, the antibody must have a charge opposite to that of the functional group attached to the ion exchange material, e.g., resin, in order to bind. For example, antibodies, which generally have an overall positive charge in the buffer pH below its pI, will bind well to cation exchange material, which contain negatively charged functional groups.

In ion exchange chromatography, charged patches on the surface of the solute are attracted by opposite charges attached to a chromatography matrix, provided the ionic strength of the surrounding buffer is low. Elution is generally achieved by increasing the ionic strength (i.e., conductivity) of the buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution).

Anionic or cationic substituents may be attached to matrices in order to form anionic or cationic supports for chromatography. Non-limiting examples of anionic exchange substituents include diethylaminoethyl (DEAE), quaternary aminoethyl (QAE) and quaternary amine (Q) groups. Cationic substitutents include carboxymethyl (CM), sulfoethyl (SE), sulfopropyl(SP), phosphate(P) and sulfonate(S). Cellulose ion exchange resins such as DE23™, DE32™, DE52™, CM-23™, CM-32™, and CM-52™ are available from Whatman Ltd. Maidstone, Kent, U.K. SEPHADEX®-based and cross-linked ion exchangers are also known. For example, DEAE-, QAE-, CM-, and SP-SEPHADEX® and DEAE-, Q-, CM- and S-SEPHAROSE® and SEPHAROSE® Fast Flow are all available from Pharmacia AB. Further, both DEAE and CM derivitized ethylene glycol-methacrylate copolymer such as TOYOPEARL™ DEAE-650S or M and TOYOPEARL™ CM-650S or M are available from Toso Haas Co., Philadelphia, Pa. In certain embodiments, an anion exchange step is accomplished using a Pall Mustang Q membrane cartridge.

A mixture comprising an antibody and impurities, e.g., HCP(s), is loaded onto an ion exchange column, such as a cation exchange column. For example, but not by way of limitation, the mixture can be loaded at a load of about 80 g protein/L resin depending upon the column used. An example of a suitable cation exchange column is a 80 cm diameter×23 cm long column whose bed volume is about 116 L. The mixture loaded onto this cation column can subsequently washed with wash buffer (equilibration buffer). The antibody is then eluted from the column, and a first eluate is obtained.

This ion exchange step facilitates the capture of the antibody of interest while reducing impurities such as HCPs. In certain aspects, the ion exchange column is a cation exchange column. For example, but not by way of limitation, a suitable resin for such a cation exchange column is CM HyperDF™ resin. These resins are available from commercial sources such as Pall Corporation. This cation exchange procedure can be carried out at or around room temperature.

4.5 Ultrafiltration/Diafiltration

Certain embodiments of the present invention employ ultrafiltration and/or diafiltration steps to further purify and concentrate the antibody sample. Ultrafiltration is described in detail in: Microfiltration and Ultrafiltration: Principles and Applications, L. Zeman and A. Zydney (Marcel Dekker, Inc., New York, N.Y., 1996); and in: Ultrafiltration Handbook, Munir Cheryan (Technomic Publishing, 1986; ISBN No. 87762-456-9). One filtration process is Tangential Flow Filtration as described in the Millipore catalogue entitled "Pharmaceutical Process Filtration Catalogue" pp. 177-202 (Bedford, Mass., 1995/96). Ultrafiltration is generally considered to mean filtration using filters with a pore size of smaller than 0.1 μm. By employing filters having such small pore size, the volume of the sample can be reduced through permeation of the sample buffer through the filter while antibodies are retained behind the filter.

Diafiltration is a method of using ultrafilters to remove and exchange salts, sugars, and non-aqueous solvents, to separate free from bound species, to remove low molecular-weight material, and/or to cause the rapid change of ionic and/or pH environments. Microsolutes are removed most efficiently by adding solvent to the solution being ultrafiltered at a rate approximately equal to the ultratfiltration rate. This washes microspecies from the solution at a constant volume, effectively purifying the retained antibody. In certain embodiments of the present invention, a diafiltration step is employed to exchange the various buffers used in connection with the instant invention, optionally prior to further chromatography or other purification steps, as well as to remove impurities from the antibody preparations.

4.6 Hydrophobic Interaction Chromatography

The present invention also features methods for producing a HCP-reduced antibody preparation from a mixture comprising an antibody and at least one HCP further comprising a hydrophobic interaction separation step. For example, a first eluate obtained from an ion exchange column can be subjected to a hydrophobic interaction material such that a second eluate having a reduced level of HCP is obtained. Hydrophobic interaction chromatography steps, such as those disclosed herein, are generally performed to remove protein aggregates, such as antibody aggregates, and process-related impurities.

In performing the separation, the sample mixture is contacted with the HIC material, e.g., using a batch purification technique or using a column. Prior to HIC purification it may be desirable to remove any chaotropic agents or very hydrophobic substances, e.g., by passing the mixture through a pre-column.

For example, in the context of batch purification, HIC material is prepared in or equilibrated to the desired equilibration buffer. A slurry of the HIC material is obtained. The antibody solution is contacted with the slurry to adsorb the antibody to be separated to the HIC material. The solution comprising the HCPs that do not bind to the HIC material is separated from the slurry, e.g., by allowing the slurry to settle and removing the supernatant. The slurry can be subjected to one or more washing steps. If desired, the slurry can be contacted with a solution of lower conductivity to desorb antibodies that have bound to the HIC material. In order to elute bound antibodies, the salt concentration can be decreased.

Whereas ion exchange chromatography relies on the charges of the antibodies to isolate them, hydrophobic interaction chromatography uses the hydrophobic properties of the antibodies. Hydrophobic groups on the antibody interact with hydrophobic groups on the column. The more hydrophobic a protein is the stronger it will interact with the column. Thus the HIC step removes host cell derived impurities (e.g., DNA and other high and low molecular weight product-related species).

Hydrophobic interactions are strongest at high ionic strength, therefore, this form of separation is conveniently performed following salt precipitations or ion exchange procedures. Adsorption of the antibody to a HIC column is favored by high salt concentrations, but the actual concentrations can vary over a wide range depending on the nature of the antibody and the particular HIC ligand chosen. Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as Ba++; Ca++; Mg++; L1+; Cs+; Na+; K+; Rb+; NH4+, while anions may be ranked in terms of increasing chaotropic effect as PO---; SO4--; CH3CO3-; Cl—; Br—; NO3—; ClO4-; I—; SCN—.

In general, Na, K or $NH_4$ sulfates effectively promote ligand-protein interaction in HIC. Salts may be formulated that influence the strength of the interaction as given by the following relationship: $(NH_4)_2SO_4$>$Na_2SO_4$>NaCl>$NH_4$Cl>NaBr>NaSCN. In general, salt concentrations of between about 0.75 and about 2 M ammonium sulfate or between about 1 and 4 M NaCl are useful.

HIC columns normally comprise a base matrix (e.g., cross-linked agarose or synthetic copolymer material) to which hydrobobic ligands (e.g., alkyl or aryl groups) are coupled. A suitable HIC column comprises an agarose resin substituted with phenyl groups (e.g., a Phenyl Sepharose™ column). Many HIC columns are available commercially. Examples include, but are not limited to, Phenyl Sepharose™ 6 Fast Flow column with low or high substitution (Pharmacia LKB Biotechnology, AB, Sweden); Phenyl Sepharose™ High Performance column (Pharmacia LKB Biotechnology, AB, Sweden); Octyl Sepharose™ High Performance column (Pharmacia LKB Biotechnology, AB, Sweden); Fractogel™ EMD Propyl or Fractogel™ EMD Phenyl columns (E. Merck, Germany); Macro-Prep™ Methyl or Macro-Prep™ t-Butyl Supports (Bio-Rad, California); WP HI-Propyl (C3)™ column (J. T. Baker, New Jersey); and Toyopearl™ ether, phenyl or butyl columns (TosoHaas, Pa.)

4.7 Exemplary Purification Strategies

In certain embodiments, primary recovery proceeds by initially employing centrifugation and filtration steps to remove cells and cell debris (including HCPs) from the production bioreactor harvest. For example, but not by way of limitation, a culture comprising antibodies, media, and cells can be subjected to centrifuguation at approximately 7000×g to approximately 11,000×g. In certain embodiments, the resulting sample supernatant is then passed through a filter train comprising multiple depth filters. In certain embodiments, the filter train comprises around twelve 16-inch Cuno™ model 30/60ZA depth filters (3M Corp.) and around three round filter housings fitted with three 30-inch 0.45/0.2 μm Sartopore™ 2 filter cartridges (Sartorius). The clarified supernatant is collected in a vessel such as a pre-sterilized harvest vessel and held at approximately 8° C. This temperature is then adjusted to approximately 20° C. prior to the capture chromatography step or steps outlined below. It should be noted that one skilled in the art may vary the conditions recited above and still be within the scope of the present invention.

In certain embodiments, primary recovery will be followed by affinity chromatography using Protein A resin. There are several commercial sources for Protein A resin. One suitable resin is MabSelect™ from GE Healthcare. An example of a suitable column packed with MabSelect™ is a column about 1.0 cm diameter×about 21.6 cm long (~17 mL bed volume). This size column can be used for bench scale. This can be compared with other columns used for scale ups. For example, a 20 cm×21 cm column whose bed volume is about 6.6 L can be used for commercial production. Regardless of the column, the column can be packed using a suitable resin such as MabSelect™

In certain aspects, the Protein A column can be equilibrated with a suitable buffer prior to sample loading. An example of a suitable buffer is a Tris/NaCl buffer, pH of about 6 to 8, including, but not limited to, about 7.2. A specific example of suitable conditions is 25 mM Tris, 100 mM NaCl, pH 7.2. Following this equilibration, the sample can be loaded onto the column. Following the loading of the column, the column can be washed one or multiple times using, e.g., the equilibrating buffer. Other washes including washes employing different buffers can be used before eluting the column. For example, the column can be washed using one or more column volumes of 20 mM citric acid/sodium citrate, 0.5 M NaCl at pH of about 6.0. This wash can optionally be followed by one or more washes using the equilibrating buffer. The Protein A column can then be eluted using an appropriate elution buffer. An example of a suitable elution buffer is an acetic acid/NaCl buffer, pH around 3.5. Suitable conditions are, e.g., 0.1 M acetic acid, pH 3.5. The eluate can be monitored using techniques well known to those skilled in the art. For example, the absorbance at $OD_{280}$ can be followed. Column eluate can be collected starting with an initial deflection of about 0.5 AU to a reading of about 0.5 AU at the trailing edge of the elution peak. The elution fraction(s) of interest can then be prepared for further processing. For example, the collected sample can be titrated to a pH of about 5.0 using Tris (e.g., 1.0 M) at a pH of about 10. Optionally, this titrated sample can be filtered and further processed.

The dynamic binding capacity (DBC) of the MabSelect™ column can be determined either by a single flow rate load or dual-flow load strategy. The single flow rate load can be evaluated at a velocity of about 300 cm/hr throughout the entire loading period. The dual-flow rate load strategy can be determined by loading the column up to about 35 mg protein/mL resin at a linear velocity of about 300 cm/hr, then reducing the linear velocity by half to allow longer residence time for the last portion of the load.

The Protein A eluate can then be further purified by employing a pH-mediated virus reduction/inactivation step. In certain embodiments this step will involve adjusting the pH of the eluate to between about 3 and about 5, including, but not limited to, about 3.5, for approximately 1 hour. The pH reduction can be facilitated using known acid preparations such as citric acid, e.g., 3 M citric acid. Exposure to acid pH reduces, if not completely eliminates, pH sensitive viral contaminants and precipitates some media/cell contaminants. Following this viral reduction/inactivation step, the pH is adjusted to about 4.9 or 5.0 using a base such as sodium hydroxide, e.g., 3 M sodium hydroxide, for about twenty to about forty minutes. This adjustment can occur at around 20° C.

In certain embodiments the pH adjusted culture is further purified using an anion exchange column. A non-limiting example of a suitable column for this step is a 60 cm diameter×30 cm long column whose bed volume is about 85 L. The column is packed with an anion exchange resin, such as Q Sepharose™ Fast Flow from GE Healthcare. The column can be equilibrated using about seven column volumes of an appropriate buffer such as Tris/sodium chloride. An example of suitable conditions are 25 mM Tris, 50 mM sodium chloride at pH 8.0. A skilled artisan may vary the conditions but still be within the scope of the present invention. The column is loaded with the collected sample from the Protein A purification step outlined above. In another aspect, the column is loaded from the eluate collected during cation exchange. Following the loading of the column, the column is washed with the equilibration buffer (e.g., the Tris/sodium chloride buffer). The flow-through comprising the antibodies can be monitored using a UV spectrophotometer at $OD_{280nm}$. This anion exchange step reduces process related impurities such as nucleic acids like DNA, and host cell proteins. The separation occurs due to the fact that the antibodies of interest do not substantially interact with nor bind to the solid phase of the column, e.g., to the Q Sepharose™, but many impurities do interact with and bind to the column's solid phase. The anion exchange can be performed at about 12° C.

In certain embodiments, the pH adjusted culture then further purified using a cation exchange column. In certain embodiments, the equilibrating buffer used in the cation exchange column is a buffer having a pH of about 5.0. An example of a suitable buffer is about 210 mM sodium acetate, pH 5.0. Following equilibration, the column is loaded with sample prepared from the primary recovery step above. The column is packed with a cation exchange resin, such as CM Sepharose™ Fast Flow from GE Healthcare. The column is then washed using the equilibrating buffer. The column is next subjected to an elution step using a buffer having a greater ionic strength as compared to the equilibrating or wash buffer. For example, a suitable elution buffer can be about 790 mM sodium acetate, pH 5.0. The antibodies will be eluted and can be monitored using a UV spectrophotometer set at $OD_{280nm}$. In a particular example, elution collection can be from upside $30D_{280nm}$ to downside $8OD_{280nm}$). It should be understood that one skilled in the art may vary the conditions and yet still be within the scope of the invention.

In certain embodiments, the pH adjusted culture, the cation exchange eluate, or the anion exchange eluate, is filtered using, e.g., a 16 inch Cuno™ delipid filter. This filtration, using the delipid filter, can be followed by, e.g., a 30-inch 0.45/0.2 μm Sartopore™ bi-layer filter cartridge. The ion exchange elution buffer can be used to flush the residual volume remaining in the filters and prepared for ultrafiltration/diafiltration.

In order to accomplish the ultratfiltration/diafiltration step, the filtration media is prepared in a suitable buffer, e.g., 20 mM sodium phosphate, pH 7.0. A salt such as sodium chloride can be added to increase the ionic strength, e.g., 100 mM sodium chloride. This ultrafiltration/diafiltration step serves to concentrate the anti-IL-13 antibodies, remove the sodium acetate and adjust the pH. Commercial filters are available to effectuate this step. For example, Millipore manufactures a 30 kD molecular weight cut-off (MWCO) cellulose ultrafilter membrane cassette. This filtration procedure can be conducted at or around room temperature.

In certain embodiments, the sample from the capture filtration step above is subjected to a second ion exchange separation step. This second ion exchange separation will, in certain embodiments, involve separation based on the opposite charge of the first ion exchange separation. For example, if an anion exchange step is employed after primary recovery, the second ion exchange chromatographic step may be a cation exchange step. Conversely, if the primary recovery step was followed by a cation exchange step, that step would be followed by an anion exchange step. In certain embodiments the first ion exchange eluate can be subjected directly to the second ion exchange chromatographic step where the first ion exchange eluate is adjusted to the appropriate buffer conditions. Suitable anionic and cationic separation materials and conditions are described above.

In certain embodiments of the instant invention the sample containing antibodies will be further processed using a hydrophobic interaction separation step. A non-limiting example of a suitable column for such a step is an 80 cm diameter×15 cm long column whose bed volume is about 75 L, which is packed with an appropriate resin used for HIC such as, but not limited to, Phenyl HP Sepharose™ from Amersham Biosciences, Upsala, Sweden. The flow-through preparation obtained from the previous anion exchange chromatography step comprising the antibodies of interest can be diluted with an equal volume of around 1.7 M ammonium sulfate, 50 mM sodium phosphate, pH 7.0. This then can be subjected to filtration using a 0.45/0.2 μm Sartopore™ 2 bi-layer filter, or its equivalent. In certain embodiments, the hydrophobic chromatography procedure involves two or more cycles.

In certain embodiments, the HIC column is first equilibrated using a suitable buffer. A non-limiting example of a suitable buffer is 0.85 M ammonium sulfate, 50 mM sodium phosphate, pH 7.0. One skilled in the art can vary the equilibrating buffer and still be within the scope of the present invention by altering the concentrations of the buffering agents and/or by substituting equivalent buffers. In certain embodiments the column is then loaded with an anion exchange flow-through sample and washed multiple times, e.g., three times, with an appropriate buffer system such as ammonium sulfate/sodium phosphate. An example of a suitable buffer system includes 1.1 M ammonium sulfate, 50 mM sodium phosphate buffer with a pH of around 7.0. Optionally, the column can undergo further wash cycles. For example, a second wash cycle can include multiple column washes, e.g., one to seven times, using an appropriate buffer system. A non-limiting example of a suitable buffer system includes 0.85 M ammonium sulfate, 50 mM sodium phosphate, pH 7.0. In one aspect, the loaded column undergoes yet a third wash using an appropriate buffer system. The column can be washed multiple times, e.g., one to three times, using a buffer system such as 1.1 M ammonium sulfate, 50 mM sodium phosphate at a pH around 7.0. Again, one skilled in the art can vary the buffering conditions and still be within the scope of the present invention.

The column is eluted using an appropriate elution buffer. A suitable example of such an elution buffer is 0.5 M ammonium sulfate, 15 mM sodium phosphate at a pH around 7.0. The antibodies of interest can be detected and collected using a conventional spectrophotometer from the upside at 3 $OD_{280\,nm}$, to downside of peak at 3 $OD_{280\,nm}$.

In certain aspects of the invention, the eluate from the hydrophobic chromatography step is subjected to filtration for the removal of viral particles, including intact viruses, if present. A non-limiting example of a suitable filter is the Ultipor DV50™ filter from Pall Corporation. Other viral filters can be used in this filtration step and are well known to those skilled in the art. The HIC eluate is passed through a pre-wetted filter of about 0.1 μm and a 2×30-inch Ultipor DV50™ filter train at around 34 psig. In certain embodiments, following the filtration process, the filter is washed using, e.g., the HIC elution buffer in order to remove any antibodies retained in the filter housing. The filtrate can be stored in a pre-sterilized container at around 12° C.

In a certain embodiments, the filtrate from the above is again subjected to ultrafiltration/diafiltration. This step is important if a practitioner's end point is to use the antibody in a, e.g., pharmaceutical formulation. This process, if employed, can facilitate the concentration of antibody, removal of buffering salts previously used and replace it with a particular formulation buffer. In certain embodiments, continuous diafiltration with multiple volumes, e.g., two volumes, of a formulation buffer is performed. A non-limiting example of a suitable formulation buffer is 5 mM methionine, 2% mannitol, 0.5% sucrose, pH 5.9 buffer (no Tween). Upon completion of this diavolume exchange the antibodies are concentrated. Once a predetermined concentration of antibody has been achieved, then a practitioner can calculate the amount of 10% Tween that should be added to arrive at a final Tween concentration of about 0.005% (v/v).

Certain embodiments of the present invention will include further purification steps. Examples of additional purification procedures which can be performed prior to, during, or following the ion exchange chromatography method include ethanol precipitation, isoelectric focusing, reverse phase HPLC, chromatography on silica, chromatography on heparin Sepharose™, further anion exchange chromatography and/or further cation exchange chromatography, chromatofocusing, SDS-PAGE, ammonium sulfate precipitation, hydroxylapatite chromatography, gel electrophoresis, dialysis, and affinity chromatography (e.g., using protein G, an antibody, a specific substrate, ligand or antigen as the capture reagent).

In certain embodiments of the present invention, the anti-IL-13 antibody is an $IgA_1$, $IgA_2$, IgD, IgE, $IgG_1$, $IgG_2$, $IgG_3$, $IgG_4$, or IgM isotype antibody comprising the heavy and light chain variable region sequences outlined in FIG. 1. In certain embodiments, the anti-IL-13 antibody is an $IgG_1$, $IgG_2$, $IgG_3$ or $IgG_4$ isotype antibody comprising the heavy and light chain variable region sequences outlined in FIG. 1.

5. Methods Of Assaying Sample Purity

5.1 Assaying Host Cell Protein

The present invention also provides methods for determining the residual levels of host cell protein (HCP) concentration in the isolated/purified antibody composition. As described above, HCPs are desirably excluded from the final target substance product, e.g., the anti-IL-13 antibody. Exemplary HCPs include proteins originating from the source of the antibody production. Failure to identify and sufficiently remove HCPs from the target antibody may lead to reduced efficacy and/or adverse subject reactions.

As used herein, the term "HCP ELISA" refers to an ELISA where the second antibody used in the assay is specific to the HCPs produced from cells, e.g., CHO cells, used to generate the antibody (e.g., anti-IL-13 antibody). The second antibody may be produced according to conventional methods known to those of skill in the art. For example, the second antibody may be produced using HCPs obtained by sham production and purification runs, i.e., the same cell line used to produce the antibody of interest is used, but the cell line is not transfected with antibody DNA. In an exemplary embodiment, the second antibody is produced using HPCs similar to those expressed in the cell expression system of choice, i.e., the cell expression system used to produce the target antibody.

Generally, HCP ELISA comprises sandwiching a liquid sample comprising HCPs between two layers of antibodies, i.e., a first antibody and a second antibody. The sample is incubated during which time the HCPs in the sample are captured by the first antibody, for example, but not limited to goat anti-CHO, affinity purified (Cygnus). A labeled second antibody, or blend of antibodies, specific to the HCPs produced from the cells used to generate the antibody, e.g., anti-CHO HCP Biotinylated, is added, and binds to the HCPs within the sample. In certain embodiments the first and second antibodies are polyclonal antibodies. In certain aspects the first and second antibodies are blends of polyclonal antibodies raised against HCPs, for example, but not limited to Biotinylated goat anti Host Cell Protein Mixture 599/626/748. The amount of HCP contained in the sample is determined using the appropriate test based on the label of the second antibody.

HCP ELISA may be used for determining the level of HCPs in an antibody composition, such as an eluate or flow-through obtained using the process described above. The present invention also provides a composition comprising an antibody, wherein the composition has no detectable level of HCPs as determined by an HCP Enzyme Linked Immunosorbent Assay ("ELISA").

5.2 Assaying Affinity Chromatographic Material

In certain embodiments, the present invention also provides methods for determining the residual levels of affinity chromatographic material in the isolated/purified antibody composition. In certain contexts such material leaches into the antibody composition during the purification process. In certain embodiments, an assay for identifying the concentration of Protein A in the isolated/purified antibody composition is employed. As used herein, the term "Protein A ELISA" refers to an ELISA where the second antibody used in the assay is specific to the Protein A employed to purify the antibody of interest, e.g., an anti-IL-13 antibody. The second antibody may be produced according to conventional methods known to those of skill in the art. For example, the second antibody may be produced using naturally occurring or recombinant Protein A in the context of conventional methods for antibody generation and production.

Generally, Protein A ELISA comprises sandwiching a liquid sample comprising Protein A (or possibly containing Protein A) between two layers of anti-Protein A antibodies, i.e., a first anti-Protein A antibody and a second anti-Protein A antibody. The sample is exposed to a first layer of anti-Protein A antibody, for example, but not limited to polyclonal antibodies or blends of polyclonal antibodies, and incubated for a time sufficient for Protein A in the sample to be captured by the first antibody. A labeled second antibody, for example, but not limited to polyclonal antibodies or blends of polyclonal antibodies, specific to the Protein A is then added, and binds to the captured Protein A within the sample. Additional non-limiting examples of anti-Protein A antibodies useful in the context of the instant invention include chicken anti-Protein A and biotinylated anti-Protein A antibodies. The amount of Protein A contained in the sample is determined using the appropriate test based on the label of the second antibody. Similar assays can be employed to identify the concentration of alternative affinity chromatographic materials.

Protein A ELISA may be used for determining the level of Protein A in an antibody composition, such as an eluate or flow-through obtained using the process described in above. The present invention also provides a composition comprising an antibody, wherein the composition has no detectable level of Protein A as determined by an Protein A Enzyme Linked Immunosorbent Assay ("ELISA").

6. Further Modifications

The antibodies of the present invention can be modified. In some embodiments, the antibodies or antigen binding fragments thereof are chemically modified to provide a desired effect. For example, pegylation of antibodies or antibody fragments of the invention may be carried out by any of the pegylation reactions known in the art, as described, e.g., in the following references: Focus on Growth Factors 3:4-10 (1992); EP 0 154 316; and EP 0 401 384, each of which is incorporated by reference herein in its entirety. In one aspect, the pegylation is carried out via an acylation reaction or an alkylation reaction with a reactive polyethylene glycol molecule (or an analogous reactive water-soluble polymer). A suitable water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (C1-C10) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under suitable conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments specific for IL-13 may generally be used to treat IL-13-related disorders of the invention by administration of the anti-IL-13 antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

An antibody or antibody portion of the invention can be derivatized or linked to another functional molecule (e.g., another peptide or protein). Accordingly, the antibodies and antibody portions of the invention are intended to include derivatized and otherwise modified forms of the human antihIL-13 antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

7. Pharmaceutical Compositions

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is desirable to include isotonic agents, e.g., sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The antibodies and antibody-portions of the invention can be incorporated into a pharmaceutical composition suitable for parenteral administration. The antibody or antibody-portions can be prepared as an injectable solution containing, e.g., 0.1-250 mg/mL antibody. The injectable solution can be composed of either a liquid or lyophilized dosage form in a flint or amber vial, ampule or pre-filled syringe. The buffer can be L-histidine approximately 1-50 mM, (optimally 5-10 mM), at pH 5.0 to 7.0 (optimally pH 6.0). Other suitable buffers include but are not limited to sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 24%). Stabilizers can be used in both liquid and lyophilized dosage forms, principally 1-50 mM L-methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

In one aspect, the pharmaceutical composition includes the antibody at a dosage of about 0.01 mg/kg-10 mg/kg. In another aspect, the dosages of the antibody include approximately 1 mg/kg administered every other week, or approximately 0.3 mg/kg administered weekly. A skilled practitioner can ascertain the proper dosage and regime for administering to a subject.

The compositions of this invention may be in a variety of forms. These include, e.g., liquid, semi-solid and solid dosage forms, such as liquid solutions (e.g., injectable and infusible solutions), dispersions or suspensions, tablets, pills, powders, liposomes and suppositories. The form depends on, e.g., the intended mode of administration and therapeutic application. Typical compositions are in the form of injectable or infusible solutions, such as compositions similar to those used for passive immunization of humans with other antibodies. One mode of administration is parenteral (e.g., intravenous, subcutaneous, intraperitoneal, intramuscular). In one aspect, the antibody is administered by intravenous infusion or injection. In another aspect, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the methods of preparation are vacuum drying and spray-drying that yields a powder of the active ingredient plus any additional desired ingredient from a previously sterile-filtered solution thereof. The proper fluidity of a solution can be maintained, e.g., by the use of a coating such as lecithin, by the maintenance of the required particle size in the case of dispersion and by the use of surfactants. Prolonged absorption of injectable compositions can be brought about by including in the composition an agent that delays absorption, e.g., monostearate salts and gelatin.

The antibodies and antibody-portions of the present invention can be administered by a variety of methods known in the art, one route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978, the entire teaching of which is incorporated herein by reference.

In certain aspects, an antibody or antibody portion of the invention may be orally administered, e.g., with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain aspects, an antibody or antibody portion of the invention is co-formulated with and/or co-administered with one or more additional therapeutic agents that are useful for treating disorders in which IL-13 activity is detrimental. For example, an anti-hIL-13 antibody or antibody portion of the invention may be co-formulated and/or co-administered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies. It will be appreciated by the skilled practitioner that when the antibodies of the invention are used as part of a combination therapy, a lower dosage of antibody may be desirable than when the antibody alone is administered to a subject (e.g., a synergistic therapeutic effect may be achieved through the use of combination therapy which, in turn, permits use of a lower dose of the antibody to achieve the desired therapeutic effect).

It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent which imparts a beneficial attribute to the therapeutic composition, e.g., an agent which effects the viscosity of the composition.

It should further be understood that the combinations which are to be included within this invention are those combinations useful for their intended purpose. The agents set forth below are illustrative and not intended to be limited. The combinations which are part of this invention can be the antibodies of the present invention and at least one additional agent selected from the lists below. The combination can also include more than one additional agent, e.g., two or three additional agents if the combination is such that the formed composition can perform its intended function.

Some combinations are non-steroidal anti-inflammatory drug(s) also referred to as NSAIDS which include drugs like ibuprofen. Other combinations are corticosteroids including prednisolone; the well known side-effects of steroid use can be reduced or even eliminated by tapering the steroid dose required when treating patients in combination with the antibodies of this invention. Non-limiting examples of therapeutic agents for rheumatoid arthritis with which an antibody, or antibody portion, of the invention can be combined to include the following: cytokine suppressive anti-inflammatory drug(s) (CSAIDs); antibodies to or antagonists of other human cytokines or growth factors, for example, TNF, LT, IL-1, IL-2, IL-6, IL-7, IL-8, IL-15, IL-16, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, or their ligands including CD 154 (gp39 or CD40L).

Some combinations of therapeutic agents may interfere at different points in the autoimmune and subsequent inflammatory cascade; examples include TNF antagonists like chimeric, humanized or human TNF antibodies, D2E7, (U.S. application Ser. No. 08/599,226 filed Feb. 9, 1996, the entire teaching of which is incorporated herein by reference), cA2 (Remicade™), CDP 571, anti-TNF antibody fragments (e.g., CDP870), and soluble p55 or p75 TNF receptors, derivatives thereof, (p75TNFRIgG (Enbrel™) or p55TNFRIgG (Lenercept), soluble IL-13 receptor (sIL-13), and also TNFα converting enzyme (TACE) inhibitors; similarly IL-1 inhibitors (e.g., Interleukin-1-converting enzyme inhibitors, such as Vx740, or IL-1RA, etc.) may be effective for the same reason. Other combinations include Interleukin 11, anti-P7s and p-selectin glycoprotein ligand (PSGL). Yet other combinations involve other key players of the autoimmune response which may act parallel to, dependent on or in concert with IL-13 function. Yet another combination includes non-depleting anti-CD4 inhibitors. Yet other combinations include antagonists of the co-stimulatory pathway CD80 (B7.1) or CD86 (B7.2) including antibodies, soluble receptors or antagonistic ligands.

The antibodies of the invention, or antigen binding portions thereof, may also be combined with agents, such as methotrexate, 6-MP, azathioprine sulphasalazine, mesalazine, olsalazine chloroquinine!hydroxychloroquine, pencillamine, aurothiomalate (intramuscular and oral), azathioprine, cochicine, corticosteroids (oral, inhaled and local injection), β-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., IRAK, NIK, IKK, p38 or MAP kinase inhibitors), IL-1β converting enzyme inhibitors (e.g., Vx740), anti-P7s, p-selectin glycoprotein ligand (PSGL), TNFα converting enzyme (TACE) inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors and the derivatives p75TNFRIgG (Enbrel™) and p55TNFRIgG (Lenercept), sIL-1 RI, sIL-1RII, sIL-6R, soluble IL-13 receptor (sIL-13)) and anti-inflammatory cytokines (e.g., IL-4, IL-10, IL-11, IL-13 and TGFα). Some combinations include methotrexate or leflunomide and in moderate or severe rheumatoid arthritis cases, cyclosporine.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. In certain embodiments it is especially advantageous to formulate parenteral compositions in dosage unit form for ease of administration and uniformity of dosage. Dosage unit form as used herein refers to physically discrete units suited as unitary dosages for the mammalian subjects to be treated; each unit comprising a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.01-20 mg/kg, or 1-10 mg/kg, or 0.3-1 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

8. Uses of the Antibodies of the Invention 8.1 Uses of Anti-IL-13 Antibody Generally Given their ability to bind to IL-13, the anti-IL-13 antibodies, or antigen-binding portions thereof, of the invention can be used to detect IL-13, in one aspect, hIL-13 (e.g., in a sample matrix, in one aspect, a biological sample, such as serum or plasma), using a conventional immunoassay, such as an enzyme linked immunosorbent assays (ELISA), an radioimmunoassay (RIA) or tissue immunohistochemistry. The invention provides a method for detecting IL-13 in a biological sample comprising contacting a sample with an antibody, or antibody portion, of the invention and detecting either the antibody bound to IL-13 or unbound antibody, to thereby detect IL-13 in the sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S, or $^{3}$H. Detection of IL-13 in a sample may be useful in a diagnostic context, for example in the diagnosis of a condition associated with increased IL-13, and/or may be useful in identifying a subject who may benefit from treatment with an anti-IL-13 antibody.

As an alternative to detection assays involving labled anti-IL-13 antibody, IL-13 can be detected in a sample by a competition immunoassay utilizing, e.g., rhIL-13 standards labeled with a detectable substance and an unlabeled anti-IL-13 antibody, such as an anti-hIL-13 antibody. In this assay, the sample, the labeled rhIL-13 standards, and the anti-hIL-13 antibody are combined and the amount of labeled rhIL-13 standard bound to the unlabeled antibody is determined. The amount of hIL-13 in the sample is inversely proportional to the amount of labeled rhIL-13 standard bound to the anti-hIL-13 antibody.

The antibodies and antibody portions of the invention are capable of neutralizing IL-13 activity in vitro and in vivo, in one aspect, a hIL-13 activity. Accordingly, the antibodies and antibody portions of the invention can be used to inhibit IL-13 activity, e.g., in a cell culture containing IL-13, in human subjects or in other mammalian subjects having IL-13 with which an antibody of the invention cross-reacts (e.g., primates such as baboon, cynomolgus and rhesus). In a one aspect, the invention provides an isolated human antibody, or antigen-binding portion thereof, that neutralizes the activity of human IL-13, and at least one additional primate IL-13 selected from the group consisting of baboon IL-13, marmoset IL-13, chimpanzee IL-13, cynomolgus IL-13 and rhesus IL-13, but which does not neutralize the activity of the mouse IL-13. In one aspect, the IL-13 is human IL-13. For example, in a cell culture containing, or suspected of containing hIL-13, an antibody or antibody portion of the invention can be added to the culture medium to inhibit hIL-13 activity in the culture.

In another aspect, the invention provides a method for inhibiting IL-13 activity in a subject suffering from a disorder in which IL-13 activity is detrimental. As used herein, the phrase "a disorder in which IL-13 activity is detrimental" is intended to include diseases and other disorders in which the presence of IL-13 in a subject suffering from the disorder has been shown to be or is suspected of being either responsible for the pathophysiology of the disorder or a factor that contributes to a worsening of the disorder. Accordingly, a disorder in which IL-13 activity is detrimental is a disorder in which inhibition of IL-13 activity is expected to alleviate the symptoms and/or progression of the disorder. Such disorders may be evidenced, e.g., by an increase in the concentration of IL-13 in a biological fluid of a subject suffering from the disorder (e.g., an increase in the concentration of IL-13 in serum, plasma, synovial fluid, etc. of the subject), which can be detected, e.g., using an anti-IL-13 antibody as described above. In one aspect, the antibodies or antigen binding portions thereof, can be used in therapy to treat the diseases or disorders described herein. In another aspect, the antibodies or antigen binding portions thereof, can be used for the manufacture of a medicine for treating the diseases or disorders described herein. There are numerous examples of disorders in which IL-13 activity is detrimental. For example, IL-13 plays a critical role in the pathology associated with a variety of diseases involving immune and inflammatory elements, including, but not limited to, respitory disorders, such as asthma and chronic obstructive pulmonary disease. Additional IL-13 related disorders include, but are not limited to: atopic disorders (e.g., atopic dermatitis and allergic rhinitis); inflammatory and/or autoimmune conditions of, the skin, gastrointestinal organs (e.g., inflammatory bowel diseases (IBD), such as ulcerative colitis and/or Crohn's disease), and liver (e.g., cirrhosis, fibrosis); scleroderma; tumors or cancers, e.g., Hodgkin's lymphoma Accordingly, anti-IL-13 antibodies or antigen-binding portions thereof, or vectors expressing same in vivo are indicated for the treatment of diseases, such as asthma or other inflammatory and/or autoimmune conditions in which there is an aberrant expression of IL-13, leading to an excess of IL-13 or in cases of complications due to exogenously administered IL-13.

8.2 Use Anti-IL-13 Antibody in Respiratory Disorders

In certain embodiments of the present invention an anti-IL-13 antibody, or antigen binding portion thereof, is employed in the treatment of one or more IL-13-associated disorders, including, but not limited to, respiratory disorders (e.g., asthma (e.g., allergic and nonallergic asthma (e.g., asthma due to infection with, e.g., respiratory syncytial virus (RSV), e.g., in younger children)), chronic obstructive pulmonary disease (COPD), and other conditions involving airway inflammation, eosinophilia, fibrosis and excess mucus production, e.g., cystic fibrosis and pulmonary fibrosis.

In certain embodiments, this application provides methods of treating (e.g., reducing, ameliorating) or preventing one or more symptoms associated with a respiratory disorder, e.g., asthma (e.g., allergic and nonallergic asthma); allergies; chronic obstructive pulmonary disease (COPD); a condition involving airway inflammation, eosinophilia, fibrosis and excess mucus production, e.g., cystic fibrosis and pulmonary fibrosis. For example, symptoms of asthma include, but are not limited to, wheezing, shortness of breath, bronchoconstriction, airway hyperreactivity, decreased lung capacity, fibrosis, airway inflammation, and mucus production. The method comprises administering to the subject an IL-13 antibody, or a fragment thereof, in an amount sufficient to treat (e.g., reduce, ameliorate) or prevent one or more symptoms. The IL-13 antibody can be administered therapeutically or prophylactically, or both. The IL-13 antagonist, e.g., the anti-IL-13 antibody, or fragment thereof, can be administered to the subject, alone or in combination with other therapeutic modalities as described herein. In certain embodiments, the subject is a mammal, e.g., a human suffering from an IL-13-associated disorder as described herein.

As noted above, IL-13 has been implicated as having a pivotal role in causing pathological responses associated with asthma. However other mediators of differential immunological pathways are also involved in asthma pathogenesis, and blocking these mediators, in addition to IL-13, may offer additional therapeutic benefit. Thus, binding proteins of the invention may be incorporated into bispecific antibody where in the bispecific antibody is capable of binding target pairs including, but not limited to, IL-13 and a pro-inflammatory cytokine, such as tumor necrosis factor-α (TNF-α). TNF-α may amplify the inflammatory response in asthma and may be linked to disease severity (McDonnell et al., Progress in Respiratory Research (2001), 31(New Drugs for Asthma, Allergy and COPD), 247-250.). This suggests that blocking both IL-13 and TNF-α may have beneficial effects, particularly in severe airway disease. In a non-limiting embodiment, the bispecfic antibody of the invention binds the targets IL-13 and TNF-α and is used for treating asthma.

In another embodiment binding proteins of the invention can be used to generate bispecific antibody molecules that bind IL-13 and IL-1beta, IL-13 and IL-9; IL-13 and IL-4; IL-13 and IL-5; IL-13 and DL-25; IL-13 and TARC; EL-13 and MDC; IL-13 and M1F; IL-13 and TGF-β; EL-13 and LHR agonist; DL-13 and CL25; IL-13 and SPRR2a; EL-13 and SPRR2b; and DL-13 and ADAMS. The present invention also provides bispecific antibodies capable of binding IL-13 and one or more targets involved in asthma selected from the group consisting of CSF1(MCSF), CSF2 (GM-CSF), CSF3 (GCSF), FGF2, IFNA1, IFNB1; IFNG, histamine and histamine receptors, EL1A, DL1B, BL2, IL3, EL4, IL5, IL6, IL7, IL8, IL9, IL1O, ELI1, IL12A, IL12B, IL14, IL15, IL16, IL17, IL18, EL19, IL-20, IL-21, IL-22, EL-23, EL-24, EL-25, IL-26, IL-27, EL-28, IL-30, EL-31, EL-32, IL-33, KtTLG, PDGFB, IL2RA, EL4R, IL5RA, IL8RA, DL8RB, IL12RB1, IL12RB2, EL13RA1, IL13RA2, IL18R1, TSLP, CCL1, CCL2, CCL3, CCL4, CCL5, CCL7, CCL8, CCL13, CCL17, CCL18, CCL19, CCL20, CCL22, CCL24,CX3CL1, CXCL1, CXCL2, CXCL3, XCL1, CCR2, CCR3, CCR4, CCR5, CCR6, CCR7, CCR8, CX3CR1, GPR2, XCR1, FOS, GATA3, JAK1, JAK3, STATE, TBX21, TGFB1, TNFSF6, YY1, CYSLTR1, FCER1A, FCER2, LTB4R, TB4R2, LTBR, and Chitinase.

EXAMPLES

1. The Production of Anti-IL-13 Antibody

A production batch of drug substance is a solution of ABT-308 monoclonal antibody obtained from the seed train, production, primary recovery and capture, and fine purification of the drug substance derived from a single cycle of the production reactor.

1.1 Media Preparation

Solutions are prepared in accordance with GMP Solution Records with purified water that meets USP/EP/JP standards. The formulated media solution is 0.1 gm filtered into the appropriately sized pre-sterilized container, bag or bioreactor. The 0.1 μm filter is integrity tested after use. The compositions of growth and production media are given in Table 2.

TABLE 2

Cell Culture Media Composition

| Raw Material | Growth Medium SR-512 | Growth Medium SR-520 | Production Medium SR-521 |
|---|---|---|---|
| PFCHO (A)-S1 | − | + | + |
| PFCHO Part A (modified) with glutamine, without NaHCO$_3$ | + | − | − |
| PFCHO Part B (ferric citrate stock solution) | + | + | + |
| Recombinant human insulin | + | + | + |
| Dextrose, anhydrous | − | + | + |
| L-glutamine | + | + | + |
| L-asparagine monohydrate | − | + | − |
| Sodium bicarbonate | + | + | + |
| HEPES, free acid | − | + | + |
| NaCl | − | + | + |
| Pluronic F-68 (Poloxamer 188, NF) | − | + | + |
| NaH$_2$PO$_4$•H$_2$O | − | + | + |
| Na$_2$HPO$_4$•7H$_2$O | − | + | + |

TABLE 2-continued

Cell Culture Media Composition

| Raw Material | Growth Medium SR-512 | Growth Medium SR-520 | Production Medium SR-521 |
|---|---|---|---|
| Bacto TC Yeastolate | + | + | + |
| Phytone Peptone | − | + | + |
| Methotrexate | + | + | + |
| 2N NaOH | − | + | + |
| 2N HCl | − | + | + |

1.2 Inoculum Expansion

Spinner flask and Biowave bag operations serve to expand the CHO cells from a single frozen vial of MCB to the desired biomass for the inoculation of a 110 L seed bioreactor. A frozen vial of Master Cell Bank is thawed and placed in growth medium (SR-512) and centrifuged. The cells are resuspended in growth medium and expanded at 37° C. and 5% $CO_2$ in disposable spinner flasks or Biowave bags of increasing volume. Duplicate 20 L wave bags are used to maximize the final cell mass expansion prior to inoculation into the seed bioreactor. When the cell density reaches $\geq 2.0 \times 10^6$ viable cells/mL from both 20 L wave bags at approximately 15-17 days, the culture is transferred into a 110 L seed bioreactor charged with growth medium SR-520 for further expansion. After inoculation, the target temperature is 37° C., and the pH is set at a target of 7.1 and controlled by addition of NaOH and $CO_2$ sparging. Dissolved oxygen (DO) in the bioreactor is controlled at target value of 40% by sparging with air and oxygen. Once the cell density reaches $\geq 2.6 \times 10^6$ viable cells/mL after approximately 2-4 days, the culture is transferred into a 3000 L production bioreactor.

1.3 Short-fill Bioreactor

A partial fill of the 3000 L production bioreactor is used to further expand the cell culture. Initially, the reactor is charged with growth medium (SR-520) and inoculated with the batch from the 110 L seed bioreactor.

During this short-fill stage, temperature, dissolved oxygen, and pH are controlled at 37° C., 40%, and 7.1, respectively. The culture pH is controlled with $CO_2$ sparging and NaOH addition. Typically, the cells grow for 2-4 days before reaching the required density of $\geq 1.6 \times 10^6$ viable cells/mL.

1.4 Production Bioreactor

Production medium SR-521 (1950 L) is added to the cell culture in the 3000 L bioreactor to initiate the production stage. Antifoam C is added to decrease foaming. The culture pH is controlled at a target value of 6.9 with on-off $CO_2$ sparging and NaOH addition. Temperature and dissolved oxygen are controlled at target values of 35° C. and 40%, respectively. The DO in the bioreactor is initially controlled at the desired value by air sparging and supplemented with pure oxygen if needed. The temperature is lowered to a target value of 33° C. when the viable cell density reaches $\geq 3.0 \times 10^6$ cells/mL, and the pH and DO are maintained at target values of 6.9 and 40%, respectively. Glucose (SR-334) is added as needed. Cultures are harvested when the cell viability drops to $\leq 50\%$.

1.5 Process Performance

The process performance and in-process test results are is given in Table 3 and Table 4, respectively.

TABLE 3

Cell Culture Process Performance for ABT-308 Manufacturing

| | | Batch No. | | |
|---|---|---|---|---|
| Seed Train | Action Limit | 55173BI | 55176BI | 57199BI |
| Viability at transfer to seed bioreactor (%) | $\geq 80$ | 96 | 98 | 96 |
| Viable cell density at transfer to seed bioreactor ($\times 10^6$/mL) | $\geq 2.0$ | 2.2 | 2.8 | 3.0 |
| Seed and Production Bioreactor | | 55448BI | 57128BI | 58067BI |
| Viable cell density at transfer to short fill ($\times 10^6$/mL) | $\geq 2.6$ | 3.0 | 3.1 | 3.8 |
| Viable cell density at end of shortfill ($\times 10^6$/mL) | $\geq 1.6$ | 1.7 | 2.1 | 2.1 |
| Viable cell density at temperature shift ($\times 10^6$/mL) | $\geq 3.0$ | 3.5 | 3.2 | 3.2 |
| Viability at Harvest (%) | $\leq 50$ | 45 | 25 | 40 |
| Harvest ABT-308 titer (g/L) | Report Value | 1.10 | 1.08 | 1.08 |

TABLE 4

Cell Culture Process In-Process Test Results

| | | Batch No. | | |
|---|---|---|---|---|
| Seed Train | Action Limit | 55173BI | 55176BI | 57199BI |
| Contamination check | No Growth | Pass | Pass | Pass |
| Seed Bioreactor | | 55448BI | 57128BI | 58067BI |
| Contamination check | No Growth | Pass | Pass | Pass |
| Production Bioreactor | | 55448BI | 57128BI | 58067BI |
| Endotoxin (EU/mL) | $\leq 5$ | <1 | <1 | <1 |
| TEM (virus-like particles/mL) | $\leq 10^8$ | Pass | Pass | Pass |
| Mycoplasma | Negative[a] | Pass | Pass | Pass |
| Adventitious virus | No evidence of viral contamination[a] | Pass | Pass | Pass |
| Q-PCR for MVM | Negative[a] | Pass | Pass | Pass |
| Contamination check | No Growth[a] | Pass | Pass | Pass |

[a]Specification

2. The Isolation and Purification of Anti-IL-13 Antibody

Primary recovery and capture operations include clarification of the harvest by filtration, capture of the antibody by Protein A affinity chromatography, and low pH viral inactivation followed by depth filtration. Fine purification operations include anion exchange chromatography, hydrophobic interaction chromatography, viral filtration, ultrafiltration/diafiltration, and final filtration, bottling and freezing.

2.1 Preparation of Solutions

Solutions are prepared in accordance with GMP Solution Records with USP purified water (USP-PW) or water for injection (WFI). Most solutions are 0.2 μm filtered into irradiated bags, autoclaved or steamed-in-place containers.

2.2 Primary Recovery and Clarification

The purpose of primary recovery by filtration is to remove cells and cell debris from the production bioreactor harvest. The unprocessed harvest is passed through a filter train consisting of depth filters, delipid depth filters and membrane filters. The clarified supernatant is collected in the harvest tank and held at 2-8° C. In-process controls for the clarified harvest include ABT-308 concentration by Poros A chromatography, bioburden and endotoxin testing.

2.3 Protein A Affinity Chromatography

The objective of Protein A affinity chromatography is to capture ABT-308 from the clarified harvest and to reduce process-related impurities. Three chromatography cycles are typically performed to process the entire harvest. The product pools from the three cycles are combined for further processing.

A 45 cm diameter×22 cm length column (35 L) is packed with MabSelect® Protein A resin (GE Healthcare) or ProSep Ultra Plus™ (Millipore) and qualified for use. The storage buffer is removed from the column by USP purified water (USP-PW) followed by 0.2 M acetic acid and finally by rinsing with USP PW. The column is equilibrated with 25 mM Tris, 100 mM NaCl, pH 7.2, then loaded with clarified harvest to a maximum of 32 g protein/L resin for the MabSelect® Protein A resin (GE Healthcare) or 45 g protein/L resin for the ProSep Ultra Plus™ (Millipore) resin. The column is washed with 25 mM Tris, 100 mM NaCl, pH 7.2, then with 20 mM sodium citrate, 0.5 M NaCl, pH 6.0, and finally washed again with 25 mM Tris, 100 mM NaCl, pH 7.2. The antibody is eluted from the column with 0.1 M acetic acid, pH 3.5. After each cycle the pH of the eluate pool is adjusted to a target of 4.1, if required. In-process controls include determination of the protein concentration by $A_{280}$, SE-HPLC, bioburden and endotoxin testing.

After the first cycle the column is regenerated with 0.2 M acetic acid and rinsed with USP-PW. After the second cycle the column is regenerated with 0.2 M acetic acid, rinsed with USP-PW, then sanitized with 0.1 M acetic acid, 20% ethanol followed by washing and short-term storage in 50 mM sodium acetate, 20% ethanol, pH 5. Following the third cycle, the column is regenerated with 0.2 M acetic acid and rinsed with USP-PW. It is then cleaned with 0.4 M acetic acid, 0.5 M NaCl, 0.1% Tween 80, followed by USP-PW, followed by 50 mM NaOH 1.0 M NaCl, then USP-PW. Finally it is sanitized with 0.1 M acetic acid, 20% ethanol followed by washing and storage in 50 mM acetic acid, 20% ethanol, pH 5.0.

2.4 Low pH Incubation and Filtration

The low pH incubation is a dedicated viral reduction step providing additional assurance of viral safety by inactivation of enveloped adventitious viruses that might be present in the Protein A eluate. The purpose of filtration after the low pH incubation is to remove any precipitates that may form during the low pH treatment.

The pH of the combined Protein A chromatography eluates is adjusted to a target value of 3.5 with 0.5 M phosphoric acid and held at 18-25° C. for 60-70 minutes. The mixture is then adjusted to pH 5 with 1 M Tris, pH 10, clarified by a combination of depth filters and membrane filters, then cooled to 10-14° C. In-process controls for the low pH treatment and filtration step include determination of the protein concentration by $A_{280}$, SE-HPLC, bioburden and endotoxin testing.

2.5 Primary Recovery and Capture Process Performance

The process performance for the primary recovery and capture operations is given in Table 5, and the results of the in-process controls are given in Table 6.

TABLE 5

Primary Recovery and Capture Process Performance

| Unit Operation | Yield (%) | | |
|---|---|---|---|
| Lot | 56136BI | 57058BI | 58207BI |
| Harvest Clarification | 80 | 81 | 87 |
| Protein A Chromatography | 103 | 109 | 99 |
| Low pH Incubation and Q Sepharose ™ Load Preparation[a] | 79[b] | 91 | 97 |

[a]Yield combined due to sampling error after low pH inactivation.
[b]The depth filter area was three-fold greater in lot 56136BI than in lots 57058BI and 58207BI. The larger filter area in lot 56136BI resulted in the decreased yield.

TABLE 6

Primary Recovery and Capture Process In-Process Test Results

| Unit Operation | In-Process Test[a] | Action Limit | 56136BI | 57058BI | 58207BI |
|---|---|---|---|---|---|
| Harvest Clarification | Bioburden | ≦15.0 CFU/mL | NA[b] | 0.0 | 0.6 |
| | Endotoxin | ≦5 EU/mL | NA[b] | <1 | <1 |
| Protein A Chromatography | SE-HPLC | ≧90.0% | 97.4 | 96.6 | 96.5 |
| | Bioburden | ≦15.0 CFU/mL | 0.0 | 0.0 | 0.0 |
| | Endotoxin | ≦5 EU/mL | <1 | <1 | <1 |
| Low pH Incubation | SE-HPLC | ≧90.0% | 98.4 | 97.9 | 98.0 |
| | Bioburden | ≦15.0 CFU/mL | 0.0 | 0.0 | 0.0 |
| | Endotoxin | ≦5 EU/mL | <1 | <1 | <1 |

[a]Bioburden and endotoxin samples taken at the start of the next unit operation.
[b]Sample not taken.

2.6 Strong Anion Exchange Chromatography

The purpose of the strong anion exchange chromatography step is to reduce process-related impurities such as host cell proteins, DNA and endotoxins. It can also serve as a viral clearance step. In certain embodiments a Q Sepharose™ FF resin column is operated in the flow-through mode in which the antibody flows through the column and the impurities remain bound to the resin, in alternative embodiments, a Mustang Q™ membrane (Pall Corp.) is employed in place of the Q Sepharose™ FF resin column. The operations are performed at 10-14° C.

A 45 cm diameter×22 cm length column (35 L) is packed with Q Sepharose™ FF resin (GE Healthcare) and qualified for use. The column is equilibrated with 25 mM Tris, 50 mM NaCl, pH 8.0. The pH of the neutralized and filtered inactivation solution is adjusted to 8.0 with 1 M Tris, pH 10, the conductivity is adjusted to 5.0-6.5, and the solution is filtered through a delipid and membrane filters. The Q Sepharose™ load is pumped through the column at a maximum load of 80 g protein/L resin. After loading, the column is washed with 25 mM Tris, 50 mM NaCl, pH 8.0 and the flow-through and wash are combined. This is the Q Sepharose™ flow-through and wash (QFTW) pool. In-process controls for the Q Sepharose™ step include concentration by $A_{280}$, SE-HPLC, bioburden and endotoxin testing.

The column is regenerated with 25 mM sodium phosphate, 1.0 M NaCl, pH 7.0, followed by a rinse with WFI, and sanitized with 1.0 M NaOH followed by a rinse with WFI. The column is then neutralized with 25 mM sodium phosphate, 1.0 M NaCl, pH 7.0 and stored in 25 mM sodium phosphate, 20% isopropanol, pH 7.0.

2.7 Hydrophobic Interaction Chromatography

The purpose of the Phenyl Sepharose™ step is the removal of ABT-308 aggregates, fragments and process-related impurities. The operations are performed at 10-14° C.

A 60 cm diameter×15 cm length column (42 L) is packed with Phenyl Sepharose™ HP resin (GE Healthcare) and qualified for use. The column is equilibrated with WFI then 20 mM sodium phosphate, 1.1 M ammonium sulfate, pH 7.0.

The Q Sepharose™ flow through and wash is diluted 1:1 (v/v) with 40 mM sodium phosphate, 2.2 M ammonium sulfate, pH 7.0. This solution, the Phenyl Sepharose™ load, is filtered through a 0.2 μm filter and loaded onto the column at a maximum load of 64 g protein/L resin. The column is washed with 25 mM sodium phosphate, 1.4 M ammonium sulfate, pH 7.0 and the ABT-308 is eluted from the column with 11 mM sodium phosphate, 0.625 M ammonium sulfate, pH 7.0. In-process controls for the Phenyl Sepharose™ step include concentration by $A_{280}$, SE-HPLC, bioburden and endotoxin testing.

The column is regenerated with WFI, then sanitized with 1 M NaOH, rinsed with WFI, and stored in 25 mM sodium phosphate, 20% isopropanol, pH 7.

2.8 Nanofiltration

Nanofiltration is a dedicated viral clearance step that provides additional assurance of viral safety by the physical removal of adventitious viruses 20 nm in diameter that might be present in the Phenyl Sepharose™ HP column eluate. The operations are performed at 10-14° C.

The Phenyl Sepharose™ HP column eluate is passed through a 0.1 μm filter and an Ultipor DV20 filter train pre-wetted with 15 mM histidine, pH 5.6. After filtration, the filter train is flushed with 15 mM histidine, pH 5.6, to recover any retained ABT-308. After use, an integrity test is performed on the DV20 filter and the filter is discarded. If the filter does not pass the integrity test, the solution may be refiltered as described above. In-process controls for the nanofiltration step include protein concentration by $A_{280}$, SE-HPLC, bioburden and endotoxin testing.

2.9 Formulation of ABT-308 Drug Substance by Ultrafiltration/Diafiltration

The purpose of the UF/DF step is the diafiltration of the drug substance into the final formulation buffer, 15 mM histidine, pH 5.6, and concentration of ABT-308. These operations are performed at 10-14° C.

The nanofiltrate is concentrated to approximately 50 g/L using 30 kDa MWCO polyether sulfone membranes, diafiltered with formulation buffer then concentrated to approximately 180 g/L. The UF system is drained of product and rinsed with diafiltration buffer to recover any product remaining in the system. The concentrate and wash are combined to produce the diafiltered ABT-308 at a concentration of approximately 120-160 g/L. The concentrated ABT-308 is filtered through membrane filters. In-process controls for the ultrafiltration/diafiltration step include concentration by $A_{280}$, SE-HPLC, bioburden and endotoxin testing.

After each run, the ultrafiltration system is flushed with WFI and cleaned with a 250 ppm sodium hypochlorite solution, then sanitized and stored in 0.1 M sodium hydroxide.

2.10 Final Filtration, Bottling and Freezing

Filtration and bottling operations are performed in a Class 100 area at 2-8° C. in a Class 100 Laminar Flow Hood. The formulated ABT-308 is filtered through a 0.2 μm filter into pre-sterilized, pyrogen-free PETG bottles. The labeled bottles are put into an empty −80° C. (nominal) freezer until frozen and then transferred to storage freezers maintained at −80° C. (nominal). In-process controls for the final filtration and bottling step include $A_{280}$, bioburden and endotoxin testing (drug substance test results).

2.11 Fine Purification Process Performance

The process performance for the primary recovery and capture operations is given in Table 7, and the results of the in-process controls are given in Table 8.

TABLE 7

Fine Purification Process Performance

| Unit Operation | Yield (%) | | |
|---|---|---|---|
| Lot | 56003BF | 57001BF | 57002BF |
| Anion Exchange Chromatography | 96 | 95 | 93 |
| Hydrophobic Interaction Chromatography | 97 | 92 | 94 |
| Nanofiltration | 98 | 98 | 96 |
| Ultrafiltration/Diafiltration | 91 | 94 | 89 |
| Final Filtration, Filling and Freezing | 93 | 97 | 100 |
| Overall yield, Capture and Fine Purification | 50 | 63 | 63 |

TABLE 8

Fine Purification In-Process Test Results

| Unit Operation | In-Process Test[a] | Action Limit | 56003BF | 57001BF | 57002BF |
|---|---|---|---|---|---|
| Anion Exchange Chromatography | SE-HPLC | ≧90.0% | 99.1 | 98.5 | 98.4 |
| | Bioburden | ≦15.0 CFU/mL | 0.0 | 0.1 | 0.0 |
| | Endotoxin | ≦5 EU/mL | <1 | <1 | <1 |
| Hydrophobic Interaction Chromatography | SE-HPLC | ≧90.0% | 99.8 | 99.7 | 99.7 |
| | Bioburden | ≦15.0 CFU/mL | 0.0 | 0.0 | 0.0 |
| | Endotoxin | ≦5 EU/mL | <1 | <1 | <1 |
| Nanofiltration | SE-HPLC | ≧90.0% | 99.8 | 99.7 | 99.7 |
| | Bioburden | ≦15.0 CFU/mL | 0.0 | 0.0 | 0.0 |
| | Endotoxin | ≦5 EU/mL | <1 | <1 | <1 |

TABLE 8-continued

Fine Purification In-Process Test Results

| Unit Operation | In-Process Test[a] | Action Limit | 56003BF | 57001BF | 57002BF |
|---|---|---|---|---|---|
| Ultrafiltration/Diafiltration | SE-HPLC | ≧90.0% | 99.7 | 99.6 | 99.6 |
| | Bioburden | ≦15.0 CFU/mL | 0.0 | 0.0 | 0.0 |
| | Endotoxin | ≦5 EU/mL | 6[b] | <1 | <1 |
| Final Filtration, Filling and Freezing | Bioburden | ≦1 CFU/mL[c] | 0[d] | 0[d] | 0[d] |
| | Endotoxin | ≦0.2 EU/mg[c] | ≦0.1[d] | ≦0.1[d] | ≦0.1[d] |

[a]Bioburden and endotoxin samples taken at the start of the next unit operation.
[b]The endotoxin result of 6 EU/mL is not considered significant because the subsequent drug substance met the specification of ≦0.2 EU/mg. In addition, lot 56003BF was an engineering run and not released for human use.
[c]Drug substance release specification.
[d]Drug substance release result.

3. Determination of Host Cell Protein Concentration in Antibody Compositions

This procedure describes the testing methodology for the determination of residual Host Cell Protein concentration in antibody samples. Enzyme Linked Immunosorbent Assay (ELISA) is used to sandwich the Host Cell Protein (Antigens) between two layers of specific antibodies. This is followed by the blocking of non-specific sites with Casein. The Host Cell Proteins are then incubated during which time the antigen molecules are captured by the first antibody (Coating Antibody). A second antibody (anti-Host Cell Protein Biotinylated) is then added which fixes to the antigen (Host Cell Proteins). Neutravidin HRP-conjugated is added which binds to the Biotinylated anti-Host Cell Protein. This is followed by the addition of K blue substrate. The chromogenic substrate is hydrolyzed by the bound enzyme conjugated antibody, producing a blue color. Reaction is stopped with 2M $H_3PO_4$, changing color to yellow. Color intensity is directly proportional to the amount of antigen bound in the well.

Preparation of 50 mM Sodium Bicarbonate (Coating Buffer), pH 9.4. To a 1 L beaker add: 900 mL Milli-Q water; 4.20 g±0.01 g Sodium Bicarbonate. Stir until completely dissolved. Adjust pH to 9.4 with 1 N NaOH. Transfer to a 1 L volumetric flask and bring to volume with Milli-Q water. Mix by inversion until homogeneous. Filter through a 0.22 µm sterile filter unit. Store at nominal 4° C. for up to 7 days from the date of preparation.

Preparation of 0.104 M $Na_2HPO_4$*$7H_2O$, 1.37 M NaCl, 0.027 M KCl, 0.0176 M $KH_2PO_4$, pH=6.8-6.9 (10×PBS). Add approximately 400 mL of Milli-Q water to a glass beaker. Add 13.94 g±0.01 g of $Na_2HPO_4$×$7H_2O$. Add 40.0 g±0.1 g of NaCl. Add 1.00 g 0.01 g of KCl. Add 1.20 g±0.01 g of $KH_2PO_4$. Stir until homogeneous. Transfer to a 500 mL volumetric flask. QS to 500 mL volume with Milli-Q water. Mix by inversion. Filter through a 0.2 µm sterile filter unit. Store at room temperature for up to 7 days.

Preparation of 1×PBS+0.1% Triton X-100, pH 7.40: (Plate Wash Buffer). In a 4 L graduated cylinder, mix 400 mL 10×PBS (step 5.2) with 3500 mL Milli-Q Water. Check pH, and adjust if necessary to 7.40±0.05 with 1 N HCl or 1 N NaOH. Bring to volume with Milli-Q water. Tightly parafilm the cylinder and mix by inversion until homogeneous. Transfer to a 4 L bottle. Remove 4 mL of the 1×PBS and discard. Add 4 mL of triton X-100 to the 3996 mL of 1×PBS. Place on stir plate and stir to completely dissolve. Filter the amount of plate wash buffer needed for dilution buffer preparation through a 0.22 µm sterile filter unit. Store at room temperature for up to 7 days.

Preparation of Coating Antibody Mixture: goat anti CHO 599/626/748 (lot # G11201 @ 1.534 mg/mL), affinity purified: NOTE: Stocks stored at nominal−80° C. in vials. Prepare aliquots. Take out one aliquot per plate at time of use. Immediately before use: Dilute antibody mixture to have a final concentration of 4 µg/mL in cold 50 mM Sodium Bicarbonate as follows. For example: add 31 µLs coating antibody mixture to 11969 µLs cold coating buffer. Mix gently by inversion.

Preparation of Biotinylated goat anti Host Cell Protein Mixture, 599/626/748 (lot# G11202 @ 0.822 mg/mL): NOTE: Stocks stored at nominal −80° C. in vials. Prepare aliquots. Take out one aliquot per plate at time of use. Immediately before use: dilute biotinylated antibody mixture to have a final concentration of 1 µg/ml in 37° C.±2° C. Casein as follows. For example: add 14.6 µLs biotinylated antibody mixture to 11985 µL 37° C.±2° C. Casein. Mix gently by inversion.

Preparation of Neutravidin-HRP. Reconstitute new lots (2 mg/vial) to 1 mg/mL as follows: Add 400 µL of Milli-Q water to the vial, then add 1600 µL 1×PBS, for a total of 2 mL. Vortex gently to mix. Store at nominal −20° C. Prepare aliquots with desired volume so that 1 aliqout per plate is used. Prepare in polypropylene tube. Qualify new lots to determine working concentration. Assign expiry of 6 months from the date of preparation. For example, if the working concentration was determined to be 0.2 µg/mL then prepare as follows. Immediately before use: thaw an aliquot of Neutravidin-HRP at room temperature. Dilute the 1 mg/mL Neutravidin solution to 0.1 mg/mL (100 µg/mL) with 37° C.±2° C. Casein. For example: Dilute X10, add 50 µL of neutravidin to 450 µL of Casein. Vortex gently to mix. Further dilute the 100 µg/mL solution to 0.2 µg/mL with 37° C.±2° C. Casein. For example: Dilute X500, add 24 µL neutravidin (100 µg/mL) to 11976 µL of Casein. Vortex gently to mix.

Preparation of 5.7 2M Phosphoric Acid (Stop Solution). Prepare a 2 M Phosphoric acid solution from concentrated phosphoric acid as follows. From the % phosphoric acid stated on the label, density (1.685 g/mL) and formula weight (98 g/mole), calculate the volume of concentrated phosphoric acid needed to prepare 500 mL of 2M phosphoric acid. Add the volume of concentrated phosphoric acid calculated above to the flask. Bring to volume with Milli-Q water and mix by inversion until homogeneous. Store at ambient temperature for up to 6 months from the date of preparation.

Preparation of Dilution Buffer (Casein diluted X100 in 1×PBS+0.1% Triton X100, pH 7.4). Dilute 37° C.±2° C. Casein X100 in 0.22 µm sterile filtered 1×PBS+0.1% Triton X100, pH 7.4 (from above). For example: Add 1 mL of 37° C.±2° C. Casein to 99 mL 0.22 µm sterile filtered 1×PBS+0.1% Triton X100, pH 7.4. Mix well. Prepare fresh for each use.

Preparation of Standards. Host cell Protein Standards (Antigen Standards) (lot # G11203 @ 1.218 mg/mL): NOTE: Stocks stored at nominal −80° C. in 70 µL aliquots. Thaw an aliquot at room temperature. Perform serial dilutions in polypropylene tubes using Dilution buffer.

Preparation of Samples. In polypropylene tubes, dilute final bulk samples to 24 mg/mL in Dilution Buffer. Record concentration. NOTE: use the solutions below to prepare spiked samples and to prepare the 12 mg/mL solutions referenced below. In polypropylene microtubes, further dilute the 24 mg/mL solutions to 12 mg/mL in Dilution Buffer. Load triplicate wells for each of the 12 mg/mL solutions on the plate for a total of 6 wells.

Preparation of Spike. In a polypropylene microtube, prepare a 10 ng/mL Host Cell Protein spike from the 20 ng/mL standard prepared above by diluting it 2× with Dilution Buffer. Load three wells for the 10 ng/mL spike solution onto the plate. Use the 20 ng/mL standard solution from step 6.1 for spiking samples.

Preparation of Spiked Samples. In polypropylene microtubes, spike 300 μL of each 24 mg/mL final bulk solution with 300 μL of the 20 ng/mL spike solution (6.1). Load triplicate wells for each spiked sample solution for a total of 6 wells.

Preparation of Control. A Control Range Must be Set for Every New Control Stock solution, before use in routine testing. Control Stock: Prepare 150 μL aliquots of a batch of ABT-308 Drug Substance Concentrate and store frozen at nominal −80° C. for up to three years.

Preparation of Working Control. Thaw an Aliquot of Control at Room temperature. In polypropylene tubes, dilute control to 24 mg/mL with Dilution Buffer. In polypropylene microtubes, further dilute the 24 mg/mL control solution with dilution buffer to 12 mg/mL. Prepare a single dilution and load control into 3 wells of the plate.

ELISA procedures. Fill plate wash bottle with plate wash buffer (refer to step 5.3, 1×PBS+0.1% Triton X−100). Prime plate washer. Check the following parameters: Parameters should be set to: Plate Type: 1 For each Cycle (a total of 5 cycles): Volume: 400 μls; Soak Time: 10 seconds; Asp. Time: 4 seconds.

Assay Procedure. Coat plates with 100 μL/well of 4 μg/mL goat coating antibody mixture in cold 50 mM Sodium Bicarbonate. Tap the side of the plate until the coating solution covers the bottom of the wells uniformly, cover with sealing tape and incubate at nominal 4° C. while shaking on plate shaker (or equivalent) at speed 3 for 18 hours±1 hour. After overnight incubation, remove plate from refrigerator and allow to equilibrate to room temperature. Shake out coating. Blot plate on paper towels. Block with 300 μL/well of 37° C.±2° C. Casein, cover with sealing tape and incubate at 37° C.±2° C. while shaking on Lab-line Environ plate shaker (or equivalent) at 80 rpm±5 rpm for 1 hour. Prepare standard, sample, control, spike, and spiked samples during blocking incubation. Wash the plate 5 times with Wash Buffer. Blot plate on paper towels. Using an 8-channel pipette, pipet 100 μL/well of standards, samples, spikes, spiked samples, and control into triplicate wells of the plate. Pipette 100 μL/well of Dilution Buffer into all empty wells of the plate to serve as blanks Cover with sealing tape and incubate at 37° C.±2° C. while shaking on Lab-line Environ plate shaker (or equivalent) at 80 rpm±5 rpm for 1 hour. Fill out a template to use as a guide when loading plate.

Plate Reader Set-Up. Set up template, entering concentrations for standards. Do not enter dilution factors for samples, control, spike, or spiked samples. Assign the wells containing diluent as blanks to be subtracted from all wells. Wash the plate 5 times with Wash Buffer. Blot plate on paper towels. Add 100 μL/well biotinylated goat antibody. Cover with sealing tape and incubate at 37° C.±2° C. while shaking on Lab-line Environ plate shaker (or equivalent) at 80 rpm±5 rpm for 1 hour. Wash the plate 5 times with Wash Buffer. Blot plate on paper towels. Add 100 μL/well Neutravidin-HRP conjugate solution. Cover with sealing tape and incubate at 37° C.±2° C. while shaking on Lab-line Environ plate shaker (or equivalent) at 80 rpm±5 rpm for 1 hour. Wash the plate 5 times with Wash Buffer. Blot plate on paper towels. Add 100 μL/well cold K-Blue substrate, cover with sealing tape and incubate at room temperature for 10 minutes (start timer as soon as substrate is added to first row), while shaking speed 3 on Lab-line titer plate shaker (or equivalent). Stop the reaction by adding 100 μL/well 2M Phosphoric Acid (Step 5.7). Place plate on a plate shaker at speed 3 for 3-5 minutes. Read plate at 450 nm.

Data Analysis and Calculations. NOTE: only samples, spikes, spiked samples, and control, with optical densities falling within the practical quantitation limit (2.5 ng/mL standard) of the standard curve and meeting the % CV or % difference criteria stated below, are accepted. If sample OD's fall below the 2.5 ng/mL standard, result should be reported as less than 2.5 ng/mL. This value should then be divided by the diluted sample concentration (12 mg/mL) to report value in ng/mg. If sample is high in host cell concentration causing the non-spiked and/or the spiked sample to be above standard curve, report value as >100 ng/mL. This value should then be divided by the diluted sample concentration (12 mg/mL) to report value in ng/mg. Consider sample value zero for spike recovery calculations when the sample is below the 2.5 ng/mL standard.

Standard Curve. Standard concentrations should be entered into the protocol template. A quadratic curve fit is used. Coefficient of determination must be =0.99 and the % CV between triplicate wells must be =20%. If this criteria is not met: One standard (1 level, 3 wells) may be dropped. If the 1.25 ng/mL is dropped, only samples and spiked samples with optical densities falling within the 2.5 ng/mL and 100 ng/mL (the remaining standard curve points) optical densities are acceptable. Additionally, for the triplicates of each standard level, if a single well is clearly contaminated or shows low binding, it may be dropped. If a well is dropped from a standard level, the remaining replicates must have a % difference=20%. The % CV for the lowest standard, which shows OD values close to the background (blanks) of the plate, should be =30%. If one well is dropped, the % difference for the remaining replicates must be =35%. If the lowest standard is dropped, only samples and spiked samples with optical densities falling within the remaining standard curve level optical densities are acceptable.

Samples. % CV should be =20% between triplicate wells. Report % CV between triplicate wells. One well from each sample dilution may be dropped. The remaining replicates must have a % difference of =20%. Note: if non-spiked sample OD is below the 2.5 ng/mL standard OD the % difference criteria does not apply to the non-spiked results. Refer to calculation above.

Calculate actual Host Cell Concentration in ng/mg from the mean (ng/mL) value as follows: CHO Host Cell Protein (ng/mg)=Mean "Non-spiked sample result (ng/mL)"_Diluted sample concentration (12 mg/mL).

Spikes. % CV should be =20% between triplicate wells. Record % CV. One well from the spike may be dropped. The remaining points must have a % difference=20%. Refer to calculation in above. Report host cell concentration in ng/mL. This result will be used in spike recovery calculations. The resulting concentration for the spike (ng/mL) must be ±20% of the theoretical spike concentration. Record result and indicate Pass or Fail. If the spike result is not within 20% of theoretical, the assay must be repeated. Mean Spike Concentration (ng/mL)×100=must be 100%±20% 10 ng/mL.

Spiked Samples. % CV should be =20% between triplicate wells. Record % CV between triplicate wells. One well from each spiked sample dilution may be dropped. The remaining replicates must have a % difference of =20%. Refer to calculation above. Report "Spiked sample result" for each dilution in ng/mL. Record % difference between duplicate dilutions. The % difference between dilutions should be =25%. These results will be used in the spike recovery calculations.

Calculate % Spike Recovery for each dilution set using the formula below: % Spike Recovery=Spiked sample value−Non-Spiked Sample Value×100 Spike Value. NOTE: (1) If non-spiked sample value OD's fall below the 2.5 ng/mL standard consider value as zero in % spike recovery calculation. % Spike recovery must be 100%±50% (50%-150%) for each dilution for each sample. Record results and Pass/Fail.

Control. % CV should be =20% between triplicate wells. Record % CV result. One well from the control may be dropped. The remaining replicates must have a % difference of =20%. Refer to calculation above. Report Host Cell concentration in the control in ng/mL. Calculate Host Cell concentration in ng/mg as follows: Host Cell Protein (ng/mg)=Control Host Cell Protein result in ng/mL.

4. Determination of Protein A Concentration in Antibody Compositions

In this ELISA, plates are coated with Chicken Anti-Protein A and incubated. Non-specific sites are blocked with casein in PBS. Plates are washed in 1×PBS+0.1% Triton X-100 to remove unbound material. Samples and Cys-rprotein A standards are diluted in 1×PBS+4.1% Triton X+10% Casein. The solutions are denatured by heating at 95° C.±2° C., separating Protein A from antibody. In certain embodiments, for example if (GE Healthcare) the solutions are then added to the plate and incubated. In alternative embodiments, for example, if the Protein A affinity step includes the use of ProSep Ultra Plus™ (Milipore), the solutions are cooled and 0.85% NaCl+12.5% 1 N Acetic Acid+0.1% Tween 20, is added to each tube (1:1) to further aid in the separation of protein A from the sample protein. The tubes are vigorously vortexed, incubated and centrifuged. The supernatants are removed and further processed. Unbound material is washed off with 1×PBS+0.1% Triton X-100. Biotinylated Chicken Anti-Protein A is added to the microtiter plate and incubated. The plate is washed to remove unbound material and Neutravidin-Peroxidase conjugate is added.

The Neutravidin will bind to the Biotinylated Chicken Anti-Protein A that has bound to the wells. The plate is washed again to remove the unbound Neutravidin and K-Blue (tetramethylbenzidine (TMB)) substrate is added to the plate. The substrate is hydrolyzed by the bound Neutravidin producing a blue color. The reaction is stopped with Phosphoric Acid, changing color to yellow. The intensity of the yellow color in the wells is directly proportional to the concentration of Protein A present in the wells.

Preparation of Reagents and Solutions Casein bottles must be warmed to 37° C.±2° C.; sonicated for 2 minutes, and aliquoted. Aliquots are to be stored at nominal 4° C. When assay is to be run, the number of casein aliquots needed, should be placed at 37° C.±2° C. The coating buffer and substrate are used cold (taken from nominal 4° C. right before use).

50 mM Sodium Bicarbonate (Coating Buffer), pH 9.4. To a 1 L beaker add: 900 mL Milli-Q water 4.20 g±0.01 g Sodium Bicarbonate. Stir until completely dissolved. Adjust pH to 9.4 with 1 N NaOH. Transfer to a 1 L volumetric flask and bring to volume with Milli-Q water. Mix by inversion until homogeneous. Filter through a 0.22 CA μm sterile filter unit. Store at nominal 4° C. for up to 7 days from the date of preparation.

104 M $Na_2HPO_4 \cdot 7H_2O$, 1.37 M NaCl, 0.027 M KCl, 0.0176 M $KH_2PO_4$, pH=6.8-6.9. (10×PBS): Add approximately 400 mL of Milli-Q water to a glass beaker. Add 13.94 g±0.01 g of $Na_2HPO_4 \times 7H_2O$. Add 40.0 g±0.1 g of NaCl. Add 1.00 g±0.01 g of KCl. Add 1.20 g±0.01 g of $KH_2PO_4$. Stir until homogeneous. Transfer to a 500 mL volumetric flask. QS to 500 mL volume with Milli-Q water. Mix by inversion. Filter through a 0.2 CA μm sterile filter unit. Store at room temperature for up to 7 days.

1×PBS+0.1% Triton X-100, pH 7.40: (Plate Wash Buffer). In a 4 L graduated cylinder, mix 400 mL 10×PBS (see above) with 3500 mL Milli-Q Water. Check pH, and adjust if necessary to 7.40±0.05 with 1 N HCl or 1 N NaOH. Bring to volume with Milli-Q water. Tightly parafilm the cylinder and mix by inversion until homogeneous. Transfer to a 4 L bottle. Remove 4 mL of the 1×PBS and discard. Add 4 mL of triton X-100 to the 3996 mL of 1×PBS. Place on stir plate and stir to completely dissolve. Store at room temperature for up to 7 days.

Chicken Anti-Protein A Coating Antibody. Take out one aliquot of antibody per plate at time of use. To qualify new lots of Chicken Anti-Protein A, it may be necessary to use and qualify Chicken Anti-Protein A-Biotin Conjugated (prepared from the same lot of coating) together. Immediately before use: Dilute antibody mixture in cold 50 mM Sodium Bicarbonate to the concentration determined during coating qualification. For example: If during qualification the concentration of coating to load on the plate was determined to be 6 μg/mL and if the stock concentration is 3000 μg/mL, then add 24 μL coating antibody to 11976 μLs cold coating buffer. Mix gently by inversion.

Biotinylated Chicken anti Protein A. Take out one aliquot of antibody per plate at time of use. To qualify new lots of Chicken Anti-Protein A-Biotin Conjugated, it may be necessary to use and qualify it with the same lot of Chicken Anti-Protein A it was prepared from. Immediately before use: Dilute biotinylated antibody in 37° C.±2° C. Casein to the concentration determined during biotinylated antibody qualification. For example: If during qualification the concentration of biotinylated antibody to load on the plate was determined to be 4 μg/mL and if the stock concentration is 1000 μg/mL, then add 48 μL biotinylated antibody to 11952 μL 37° C.±2° C. Casein. Mix gently by inversion.

Neutravidin-HRP. Reconstitute new lots (2 mg/vial) to 1 mg/mL as follows: Add 400 μL of Milli-Q water to the vial, then add 1600 μL 1×PBS, for a total of 2 mL. Vortex gently to mix. Store at nominal −80° C. Prepare aliquots with desired volume so that 1 aliqout per plate is used. Prepare in polypropylene tube. Assign expiration date of 6 months from the date of preparation. For example, if the working concentration was determined to be 0.1 μg/mL then prepare as follows. Immediately before use, thaw an aliquot of Neutravidin-HRP at room temperature. Dilute the 1 mg/mL Neutravidin solution to 0.01 mg/mL (10 μg/mL) with 37° C.±2° C. Casein. For example: Dilute X10, add 50 μL of neutravidin to 450 μL of Casein. Vortex gently to mix, X10 again, add 100 μL of ×10 neutravidin to 900 μL of Casein. Vortex gently to mix. Further dilute the 10 μg/mL solution to 0.1 μg/mL with 37° C.±2° C. Casein. For example: Dilute X100, add 120 μL neutravidin (10 μg/mL) to 11880 μL of Casein. Invert several times gently to mix.

Stop Solution (Purchased 1 N Phosphoric Acid is used.) Store at ambient temperature for up to 1 year from the date of receipt. Dilution Buffer (1×PBS+4.1% Triton X100+10%

Casein, pH 7.4). Add 86 mL of 1×PBS+0.1% Triton X100, pH 7.4 (from Step 5.3) to a beaker or flask, add 4 mL of Triton X-100, and 10 mL of Blocker Casein in PBS, and stir to dissolve/mix. It may take 20 to 30 minutes to dissolve triton. This equals a 1×PBS+4.1% Triton X100+10% Casein, pH 7.4 solution. Filter through a 0.22 CA μm sterile filter unit. Prepare fresh for each use. This is enough for 1 plate.

Protein A Standards (Antigen Standards). NOTE: Stocks stored at nominal −20° C. in 70 μL aliquots. Thaw an aliquot on ice. Perform serial dilutions according to the examples in the table below polypropylene tubes using Dilution buffer (see above) using the concentration stated on the manufacturers COA: For example if COA states stock concentration is 2.1 mg/mL (2100000 ng/mL) then: Thaw samples on ice. In polypropylene microcentrifuge tubes, dilute final bulk samples to 20 mg/mL in Dilution Buffer (above). Perform 2 separate dilutions. Record concentration. Use the solutions below to prepare spiked samples and to prepare the 10 mg/mL solutions. For example: Conc. (mg/mL) Vol. μL of X mg/mL solution Vol. of diluent (4) Serial Dilution From 120 stock sample. In polypropylene microcentrifuge tubes, further dilute the 20 mg/mL solutions to 10 mg/mL in Dilution Buffer.

Preparation of Spike. In a polypropylene microcentrifuge tube, prepare a 0.296 ng/mL Protein A spike from the 0.593 ng/mL standard prepared above in Step 6.1 by diluting it 2× with Dilution Buffer. Perform a single dilution. Triplicate wells for the 0.296 ng/mL spike solution will be loaded onto the plate. Use the 0.593 ng/mL standard solution from Step 6.1 for spiking samples.

Preparation of Spiked Samples. in Polypropylene Microcentrifuge Tubes, Spike 500 μL of each 20 mg/mL final bulk solution with 500 μL of the 0.593 ng/mL spike solution. Hold for denaturation. Triplicate wells for each spiked sample solution will be loaded on the plate for a total of 6 wells.

Preparation of Control. Obtain a lot of ABT-308 Drug Substance. Prepare 150 μL aliquots and store frozen at nominal −80° C. for three years from the date aliquoted.

Working Control: Thaw an aliquot of control on ice. In a polypropylene microcentrifuge tube, dilute control to 10 mg/mL with Dilution Buffer to have a final volume of 1000 μLs. Prepare a single dilution. Hold for denaturation. Triplicate wells of control will be loaded onto the plate.

Denaturation. For plate blanks, add 1000 μL of dilution buffer to microcentrifuge tubes equal to the number of blanks that will be run on the plate. The caps of the tubes may be parafilmed to prevent them from popping open during heating or a second rack may be placed on top of them to keep caps closed. Heat standards, non-spiked samples, spiked samples, spike, blanks, and control, at 95° C.±2° C. for 15 minutes. Remove parafilm from tubes during cooling, if used. Allow to cool for 15 minutes, and centrifuge for 5 minutes at approximately 10000 rpm. Transfer 700 μL of the supernatant into microtubes to load on plate. Be careful not to disturb the triton/protein pellet.

Plate Washer Instructions and Waterbath Set-Up. Fill plate wash bottle with plate wash buffer (refer to Step 5.3, 1×PBS+0.1% Triton X-100). Prime plate washer. Check the following parameters: Parameters should be set to: Plate Type: 1 For each Cycle (a total of 4 cycles): Asp speed: 10 mm/s; Volume: 400 μls; Soak Time: 5 seconds; Asp. Time: 6 seconds. Turn on waterbath and set to 95° C. Allow waterbath temperature to equilibrate to 95° C.±2° C. for at least 30 minutes.

Assay Procedure: A Checklist can be used as a guide by checking off steps as they are completed. Additionally, record all equipment used during the assay. The amount of Casein aliquots to be used for each day the assay will be run must be placed at 37° C.±2° C. The coating Buffer and substrate are used cold. Prepare standard, sample, control, spike, and spiked samples prior to and during blocking incubation. It may take longer than the 1 hour block incubation to prepare dilutions, transfer to eppendorf tubes, denature for 15 minutes, cool for 15 minutes, centrifuge for 5 minutes, and to transfer to microtubes. Allow at least 40 minutes prior to blocking plates. Samples, Spiked Samples, Standards, Control, Assay Spike, and Blanks, are loaded on the plate horizontally from rows B through G using a 12 channel pipette. Standards are loaded from high to low concentration. Plate coating, biotin addition, neutravidin addition, substrate addition, and stop solution addition are done vertically from columns 2 through 11.

Coat plates with 100 μL/well of coating antibody in cold 50 mM Sodium Bicarbonate. Tap the side of the plate until the coating solution covers the bottom of the wells uniformly, cover with sealing tape and incubate at nominal 4° C. while shaking on plate shaker (or equivalent) at speed 3.

After overnight incubation, remove plate from refrigerator and allow to equilibrate to room temperature. Shake out coating. Blot plate on paper towels. Block with 300 μL/well of 37° C.±2° C. Casein, cover with sealing tape and incubate at 37° C.±2° C. while shaking on Lab-line Environ plate shaker (or equivalent) at 80 rpm±5 rpm for 1 hour±10 minutes.

Prepare standard, sample, control, spike, and spiked samples prior to and during blocking incubation. Wash the plate 4 times with Wash Buffer. Blot plate on paper towels. Using an 8-channel pipette, pipet 100 μL/well of denatured standards, samples, spikes, spiked samples, blanks, and control into triplicate wells of the plate. The outside wells of the plate are not used, add non-treated dilution buffer to these wells. Cover with sealing tape and incubate at 37° C.±2 C while shaking on Lab-line Environ plate shaker (or equivalent) at 80 rpm±5 rpm for 2 hours. Fill out a template to use as a guide when loading plate.

Plate Reader Set-Up. Wash the plate 4 times with Wash Buffer. Blot plate on paper towels. Add 100 μL/well biotinylated antibody. Cover with sealing tape and incubate at 37° C.±2° C. while shaking on Lab-line Environ plate shaker (or equivalent) at 80 rpm±5 rpm for 1 hour.

Wash the plate 4 times with Wash Buffer. Blot plate on paper towels. Add 100 μL/well Neutravidin-HRP conjugate solution. Start timer as soon as neutravidin is added to the last row. Cover with sealing tape and incubate at 37° C.±2° C. while shaking on Lab-line Environ plate shaker (or equivalent) at 80 rpm±5 rpm for 30 minutes. Wash the plate 4 times with Wash Buffer. Blot plate on paper towels. Add 100 μL/well cold K-Blue substrate, cover with sealing tape and incubate at room temperature for 10 minutes (start timer as soon as substrate is added to first row), while shaking speed 3 on Lab-line titer plate shaker (or equivalent). Stop the reaction by adding 100 μL/well 1 N Phosphoric Acid. Place plate on a plate shaker at speed 3 for 3 minutes. Read plate at 450 nm.

Data Analysis and Calculations NOTE: Only samples, spikes, spiked samples, and control, with optical densities falling within the practical quantitation limit of the standard curve and meeting the % CV or % difference criteria stated below, are accepted. If sample OD's fall below standard curve, result should be reported as less than 0.18 ng/mL (assay LOQ). This value should then be divided by the diluted sample concentration (10 mg/mL) to report value in ng/mg. If the sample is high in Protein A concentration causing the non-spiked and/or the spiked sample to be above standard curve (2 ng/mL), then dilute further to be within the standard curve. This value should then be divided by the diluted sample concentration to report value in ng/mg. For spike recovery calculations, subtract non-spiked sample value (ng/mL) from spiked sample value (ng/mL) even when the non-spiked sample value (ng/mL) is below the curve. If value is negative or 'range' is obtained then consider non-spiked sample as zero for spike recovery calculations.

Standard Curve. Standard concentrations should be entered into the protocol template. A quadratic curve fit is used. Coefficient of determination must be =0.99 and the % CV between triplicate wells must be =20%. If this criteria is not met: One standard (1 level, 3 wells) may be dropped. If the 0.18 ng/mL is dropped, only samples and spiked samples with optical densities falling within the 0.26 ng/mL and 2 ng/mL (the remaining standard curve points) optical densities are acceptable. Additionally, for the triplicates of each standard level, if a single well is clearly contaminated or shows low binding, it may be dropped. If a well is dropped from a standard level, the remaining replicates must have a % difference=20%. The % CV for the lowest standard, which shows OD values close to the background (blanks) of the plate, should be =30%. If one well is dropped, the % difference for the remaining replicates must be =35%. If the lowest standard is dropped, only samples and spiked samples with optical densities falling within the remaining standard curve level optical densities are acceptable.

Calculate % Difference as follows: % Difference=(Abs. (result dilution 1−result dilution 2)/mean value)×100%. The assay must be repeated if the standards do not meet the above criteria. Report % CV and/or % difference values and standard Curve Coefficient of determination results.

Samples. % CV should be =20% between triplicate wells. Report % CV between triplicate wells. One well from each sample dilution may be dropped. The remaining replicates must have a % difference of =20%. Note: If non-spiked sample OD is below lowest standard OD the % difference criteria does not apply to the non-spiked results. Refer to calculation above.

Report "Non-spiked sample result" for each dilution in ng/mL. These values will be used in spike recovery calculations. Calculate the mean "Non-spiked sample result (ng/mL)" and the % difference between dilutions. Report results. % Difference between dilutions must be =25%. Calculate actual Protein A Concentration in ng/mg from the mean (ng/mL) value as follows: Protein A (ng/mg)=Mean "Non-spiked sample result (ng/mL)" Diluted sample concentration (10 mg/mL). Record result.

Spikes. % CV should be =20% between triplicate wells. Record % CV. One well from the spike may be dropped. The remaining points must have a % difference=20%. Refer to calculation above. Report protein A concentration in ng/mL. This result will be used in spike recovery calculations. The resulting concentration for the spike (ng/mL) must be ±20% of the theoretical spike concentration. Record result and indicate Pass or Fail. If the spike result is not within 20% of theoretical, the assay must be repeated. Mean Spike Concentration (ng/mL)×100=must be 100%±20% 0.296 ng/mL Spiked Samples. % CV should be =20% between triplicate wells. Record % CV between triplicate wells. One well from each spiked sample dilution may be dropped. The remaining replicates must have a % difference of =20%. Refer to calculation above. Report "Spiked sample result" for each dilution in ng/mL. Record % difference between duplicate dilutions. The % difference between dilutions should be =25%. These results will be used in the spike recovery calculations. Calculate % Spike Recovery for each dilution set using the formula below: % Spike Recovery=Spiked sample value−Non-Spiked Sample Value×100. Spike Value NOTE: For spike recovery calculations, subtract non-spiked sample value (ng/mL) from spiked sample value (ng/mL) even when the non-spiked sample value (ng/mL) is below the curve. If value is negative or 'range' is obtained then consider non-spiked sample as zero for spike recovery calculations. % Spike recovery must be 100%±50% (50%-150%) for each dilution for each sample. Record results and Pass/Fail.

Control. % CV should be =20% between triplicate wells. Record % CV result. One well from the control may be dropped. The remaining replicates must have a % difference of =20%.

TABLE 9

Residual Host Cell Protein and Protein A Assay Results

| Batch# | Protein A (ng/mg) | Host Cell Protein (ng/mg) |
|---|---|---|
| 56003BF | 1.01 | <0.14 |
| 57001BF | 1.58 | <0.14 |
| 57002BF | 1.68 | <0.14 |
| 88018BF | <0.29 | <0.14 |
| 89001BF | <0.29 | <0.14 |
| 90006BF | <0.29 | <0.14 |
| 90009BF | <0.29 | <0.14 |

TABLE 10

Residual Host Cell Protein and Protein A Assay Results: In Process Samples

| | Process Step | | | | | |
|---|---|---|---|---|---|---|
| | Protein A | | Anion Exchange | | Hydrophobic Interaction | |
| Batch* | Protein A (ng/mg) | HCP (ng/mg) | Protein A (ng/mg) | HCP (ng/mg) | Protein A (ng/mg) | HCP (ng/mg) |
| 88018BF | 9.55 | 768 | 0.79 | 4 | 0.17 | ≦0.120 |
| 89001BF | 8.64 | 797 | 0.41 | 3 | 0.11 | ≦0.128 |
| 90006BF | 9.67 | 914 | 0.50 | 3 | 0.16 | ≦0.118 |
| 90009BF | 7.86 | 798 | 0.50 | 3 | 0.18 | ≦0.124 |

Various publications are cited herein, the contents of which are hereby incorporated by reference in their entireties.

What is claimed is:

1. A method for producing a host cell-protein (HCP) reduced antiIL-13 antibody, or antigen-biding fragment thereof, preparation from a sample mixture comprising an anti-IL-13 antibody, or antigen-binding fragment thereof, and at least one HCP, said method comprising:
   (a) contacting said sample mixture to Protein A affinity chromatography resin, washing said affinity chromatomphy resin with a buffer comprising 0.5 M NaCl, 20 mM Na citrate, at pH 6, and a buffer comprising 25 mM Tris, 100 mM NaCl, pH 7.2 and collecting an affinity chromatography sample;
   (b) subjecting said affinity chromatography sample to a reduction in pH thus forming a reduced pH sample, wherein said reduction in pH is from about 3 to about 4;
   (c) adjusting said reduced pH sample to a pH of about 4.5 to about 6.5 and contacting said adjusted pH sample to an ion exchange resin and collecting an ion exchange sample;
   (d) contacting said ion exchange sample to a hydrophobic interactive chromatography (HIC) resin and collecting an HIC sample, wherein said HIC sample comprises said HCP-reduced antibody, or antigen binding portion thereof, preparation.

2. The method of claim 1, wherein said reduction in pH is accomplished by admixing a suitable acid with said sample mixture, and wherein said suitable acid is selected from the group consisting of citric acid, acetic acid, and caprylic acid.

3. The method of claim 1, wherein said Protein A resin comprises Protein A coupled to crosslinked agarose beads.

4. The method of claim 1, wherein said ion exchange sample is applied to a cation exchange resin and a cation exchange sample is collected prior to application to the hydrophobic interaction chromatography resin.

5. The method of claim 1, wherein said ion exchange resin is a cation exchange resin.

6. The method of claim 5, wherein said cation exchange comprises a substituted matrix wherein the substituents are selected from the group consisting of $SO_3^-$, carboxymethyl, sulfoethyl, sulfopropyl, phosphate and sulfonate.

7. The method of claim 6, wherein said substituent is $SO_3^-$.

8. The method of claim 1, wherein said ion exchange resin is an anion exchange resin.

9. The method of claim 8, wherein said anion exchange resin comprises a substituted matrix wherein the substituents are selected from the group consisting of diethylaminoethyl, quaternary aminoethyl, and quaternary amine groups.

10. The method of claim 9, wherein said substituent is a quaternary amine.

11. The method of claim 1, wherein said HIC resin comprises a substituted matrix wherein the substituents consist of one or more hydrophobic groups.

12. The method of claim 11, wherein said substituents are selected from the group consisting of alkyl-, aryl-groups, and a combination thereof.

13. The method of claim 12, wherein said substituents are selected from the group consisting of: phenyl, 3-octoxypropane-1,2-diol and ether, propyl, methyl, or butyl groups.

14. The method of claim 13, wherein said resin comprises an agarose matrix comprising phenyl substituents.

15. The method of claim 1, further comprising a filtration step, wherein said HIC sample is subjected to filtration to remove viral particles and to facilitate buffer exchange.

16. The method of claim 10, wherein said anti-IL-13 antibody or antigen-binding portion thereof is a humanized antibody, a chimeric antibody, or a multivalent antibody.

17. The method of claim 16, wherein said anti-IL-13 antibody or antigen-binding portion thereof is a humanized antibody.

18. The method of claim 1, wherein said preparation is substantially free of HCPs.

19. The method of claim 1 further comprising a depth filtration step.

* * * * *

SEQUENCE LISTING

<160> NUMBER OF SEQ ID NOS: 2

<210> SEQ ID NO 1
<211> LENGTH: 123
<212> TYPE: PRT
<213> ORGANISM: Homo sapiens -continued

```
<400> SEQUENCE: 1

Glu Val Thr Leu Arg Glu Ser Gly Pro Gly Leu Val Lys Pro Thr Gln
1               5                   10                  15

Thr Leu Thr Leu Thr Cys Thr Leu Tyr Gly Phe Ser Leu Ser Thr Ser
            20                  25                  30

Asp Met Gly Val Asp Trp Ile Arg Gln Pro Pro Gly Lys Gly Leu Glu
        35                  40                  45

Trp Leu Ala His Ile Trp Trp Asp Asp Val Lys Arg Tyr Asn Pro Ala
    50                  55                  60

Leu Lys Ser Arg Leu Thr Ile Ser Lys Asp Thr Ser Lys Asn Gln Val
65                  70                  75                  80

Val Leu Lys Leu Thr Ser Val Asp Pro Val Asp Thr Ala Thr Tyr Tyr
                85                  90                  95

Cys Ala Arg Thr Val Ser Ser Gly Tyr Ile Tyr Tyr Ala Met Asp Tyr
            100                 105                 110

Trp Gly Gln Gly Thr Leu Val Thr Val Ser Ser
            115                 120

<210> SEQ ID NO 2
<211> LENGTH: 107
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Phe Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Tyr Cys Gln Gln Gly Asn Thr Leu Pro Leu
                85                  90                  95

Thr Phe Gly Gly Gly Thr Lys Val Glu Ile Lys
            100                 105
```